United States Patent
Park et al.

(10) Patent No.: US 10,242,877 B2
(45) Date of Patent: Mar. 26, 2019

(54) ALUMINUM COMPOUND AND METHODS OF FORMING THIN FILM AND FABRICATING INTEGRATED CIRCUIT DEVICE BY USING THE SAME

(71) Applicant: SAMSUNG ELECTRONICS CO., LTD., Suwon-si, Gyeonggi-do (KR)

(72) Inventors: Gyu-hee Park, Hwaseong-si (KR); Jae-soon Lim, Seoul (KR); Youn-joung Cho, Hwaseong-si (KR)

(73) Assignee: Samsung Electronics Co., Ltd., Suwon-Si, Gyeonggi-do (KR)

( * ) Notice: Subject to any disclaimer, the term of this patent is extended or adjusted under 35 U.S.C. 154(b) by 0 days.

(21) Appl. No.: 15/423,027

(22) Filed: Feb. 2, 2017

(65) Prior Publication Data
US 2018/0019135 A1 Jan. 18, 2018

(30) Foreign Application Priority Data
Jul. 14, 2016 (KR) .......... 10-2016-0089206

(51) Int. Cl.
| H01L 21/00 | (2006.01) |
|---|---|
| H01L 21/285 | (2006.01) |
| H01L 49/02 | (2006.01) |
| H01L 27/11582 | (2017.01) |
| H01L 29/66 | (2006.01) |

(52) U.S. Cl.
CPC .. H01L 21/28556 (2013.01); H01L 27/11582 (2013.01); H01L 28/60 (2013.01); H01L 29/66795 (2013.01)

(58) Field of Classification Search
CPC ......... H01L 21/28556; H01L 27/11582; H01L 28/60; H01L 29/66795
See application file for complete search history.

(56) References Cited

U.S. PATENT DOCUMENTS

| 6,743,475 B2 | 6/2004 | Skarp et al. |
| 7,374,964 B2 | 5/2008 | Ahn et al. |
| 7,462,559 B2 | 12/2008 | Millward |
| 7,544,990 B2 * | 6/2009 | Bhattacharyya ....... B82Y 10/00 257/314 |
| 7,615,250 B2 | 11/2009 | Peters et al. |
| 8,455,672 B2 | 6/2013 | Gordon et al. |
| 8,835,273 B2 | 9/2014 | Chen et al. |
| 9,064,900 B2 * | 6/2015 | Goldbach ......... H01L 29/66795 |

(Continued)

FOREIGN PATENT DOCUMENTS

| JP | 2013-166965 A | 8/2013 |
| KR | 10-2008-0090870 A | 10/2008 |
| KR | 10-1221861 B1 | 1/2013 |

*Primary Examiner* — Richard A Booth
(74) *Attorney, Agent, or Firm* — Lee & Morse, P.C.

(57) ABSTRACT

Provided are an aluminum compound represented by General Formula (I), a method of forming a thin film, and a method of fabricating an integrated circuit device.

General Formula (I)

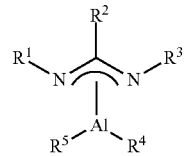

16 Claims, 37 Drawing Sheets

(56) References Cited

U.S. PATENT DOCUMENTS

| | | |
|---|---|---|
| 9,269,574 B2 | 2/2016 | Hung et al. |
| 2005/0239297 A1 | 10/2005 | Senzaki et al. |
| 2011/0287612 A1* | 11/2011 | Lee .................. H01L 27/11565 |
| | | 438/478 |
| 2013/0078454 A1 | 3/2013 | Thompson et al. |
| 2015/0146341 A1 | 5/2015 | Fuchigami et al. |

* cited by examiner

ALUMINUM COMPOUND AND METHODS OF FORMING THIN FILM AND FABRICATING INTEGRATED CIRCUIT DEVICE BY USING THE SAME

CROSS-REFERENCE TO RELATED APPLICATION

Korean Patent Application No. 10-2016-0089206, filed on Jul. 14, 2016, in the Korean Intellectual Property Office, and entitled: "Aluminum Compound and Methods of Forming Thin Film and Fabricating Integrated Circuit Device by Using the Same," is incorporated by reference herein in its entirety.

BACKGROUND

1. Field

Embodiments relate to an aluminum compound and methods of forming a thin film and fabricating an integrated circuit device by using the same.

2. Description of the Related Art

Due to the development of electronic technology, downscaling of semiconductor devices is being quickly performed in recent years, and thus, patterns constituting electronic devices are becoming finer.

SUMMARY

Embodiments are directed to an aluminum compound represented by General Formula (I):

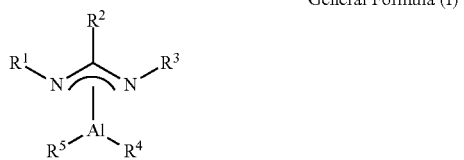

General Formula (I)

wherein $R^1$ and $R^3$ are each independently a C4 to C10 branched alkyl, alkenyl, or alkynyl group, or a C4 to C20 substituted or unsubstituted aromatic or alicyclic hydrocarbon group; and $R^2$, $R^4$, and $R^5$ are each independently a C1 to C10 linear or branched alkyl, alkenyl, or alkynyl group, or a C6 to C20 substituted or unsubstituted aromatic or alicyclic hydrocarbon group.

Embodiments are also directed to a method of forming a thin film, the method including forming an aluminum-containing film on a substrate by using the aluminum compound represented by General Formula (I).

Embodiments are also directed to a method of fabricating an integrated circuit device, the method including: forming a lower structure on a substrate, and forming an aluminum-containing film on the lower structure at a temperature of about 300° C. to about 600° C. by using the aluminum compound represented by General Formula (I).

BRIEF DESCRIPTION OF THE DRAWINGS

Features will become apparent to those of skill in the art by describing in detail example embodiments with reference to the attached drawings in which:

FIG. 6A is a plan view of an integrated circuit device, FIG. 6B is a perspective view of the integrated circuit device of FIG. 6A, and FIG. 6C shows cross-sectional views of the integrated circuit device, which are respectively taken along lines X-X' and Y-Y' of FIG. 6A;

DETAILED DESCRIPTION

Figure 1:
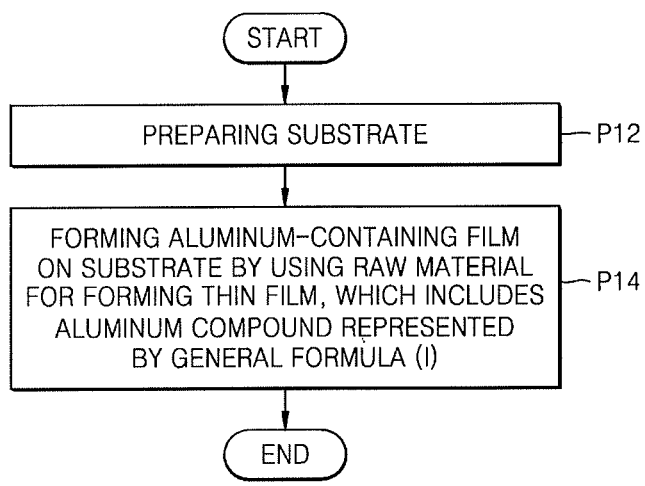
FIG. 1 illustrates a flowchart of a method of forming a thin film according to an example embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

As used herein, the term "alkyl group" refers to saturated functional groups containing exclusively carbon and hydrogen atoms. In addition, the term "alkyl group" refers to linear, branched, or cyclic alkyl groups. Examples of linear alkyl groups may include a methyl group, an ethyl group, a propyl group, a butyl group, and the like, without being limited thereto. Examples of branched alkyl groups may include a t-butyl group, without being limited thereto. Examples of cyclic alkyl groups may include a cyclopropyl group, a cyclopentyl group, a cyclohexyl group, and the like, without being limited thereto. As used herein, the abbreviation "Me" refers to a methyl group; the abbreviation "Et" refers to an ethyl group; the abbreviation "iPr" refers to an isopropyl group; and the abbreviation "tBu" refers to a tertiary-butyl group. As used herein, the term "room temperature" refers to a temperature ranging from about 20° C. to about 28° C. and may vary with the seasons.

According to an example embodiment, an aluminum compound may be represented by General Formula (I):

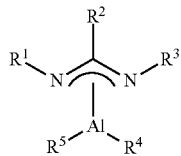

General Formula (I)

wherein $R^1$ and $R^3$ are each independently a C4 to C10 branched alkyl, alkenyl, or alkynyl group, or a C4 to C20 substituted or unsubstituted aromatic or alicyclic hydrocarbon group; and $R^2$, $R^4$, and $R^5$ are each independently a C1 to C10 linear or branched alkyl, alkenyl, or alkynyl group, or a C6 to C20 substituted or unsubstituted aromatic or alicyclic hydrocarbon group. The aluminum compound represented by General Formula (I) may have a thermal decomposition temperature of about 350° C. to about 500° C.

In an example embodiment, $R^1$ and $R^3$ of the aluminum compound represented by General Formula (I) each includes a tertiary carbon atom (a carbon atom bonded to three other carbon atoms) bonded directly to the illustrated nitrogen atom. As an example, a tertiary-butyl group may be used for $R^1$ and/or $R^3$. When $R^1$ and $R^3$ of the aluminum compound represented by General Formula (I) each includes a tertiary carbon atom bonded directly to the nitrogen atom, the aluminum compound represented by General Formula (I) has no hydrogen atom at a carbon in a β-position with respect to an Al atom.

In an example embodiment, $R^1$ and $R^3$ of the aluminum compound represented by General Formula (I) may have no hydrogen atom at a (β-position with respect to an Al atom. $R^1$ and $R^3$ in General Formula (I) may be selected as functional groups having no hydrogen atom at the β-position with respect to the Al atom that is a central metal atom, which may help improve thermal stability of the aluminum compound.

If a hydrogen atom is present at the β-position, β-H elimination may be induced with increasing temperature. Thus, a bond between a central metal (aluminum) and an N ligand (Al-N) may be broken. As a result, the thermal decomposition temperature of the aluminum compound may be reduced. If the thermal decomposition temperature of the aluminum compound is reduced, the thermal stability of the aluminum compound may be deteriorated, and thus, a process temperature upon a process of forming a thin film by using the aluminum compound may be limited to a relatively low temperature.

An aluminum-containing film is used for various purposes in semiconductor devices, and the reliability of semiconductor devices may depend upon film properties of an aluminum-containing film. For example, when an aluminum oxide film is formed by an atomic layer deposition (ALD) process, an aluminum compound used as an aluminum precursor may be vaporized to form the aluminum oxide film. In addition, to form an aluminum oxide film having excellent thin film properties, a process temperature upon an ALD process may be set relatively high. Thus, if an aluminum compound in use has low thermal stability, the aluminum compound may be thermally decomposed during the ALD process performed at a relatively high temperature, for example, a temperature of about 400° C. or more. As a result, instead of a self-limiting reaction required for ALD, chemical vapor deposition (CVD) may primarily occur. Thus, an aluminum oxide film having desired film properties may not be obtained. If the temperature upon the ALD process is set low in order to avoid such a result, the thin film may not have a good quality that is free from impurities and may not provide sufficient step coverage in the case of a high aspect ratio.

On the other hand, the aluminum compound according to the present example embodiment may exhibit a relatively high thermal decomposition temperature of about 350° C. to about 500° C. Thus, ALD deposition properties may be satisfied even though an ALD process is performed at a temperature of about 400° C. or more by using the aluminum compound according to the present example embodiment. In addition, an aluminum-containing film may be formed by a relatively high temperature process, and as a result, undesired impurities may be prevented from remaining in the obtained aluminum-containing film. Therefore, the aluminum-containing film may exhibit improved film properties and improved step coverage even in the case of a high aspect ratio.

In addition, the aluminum compound according to the present example embodiment may provide sufficient volatility to perform an ALD process, and is in a liquid state at room temperature due to a low melting point thereof. Therefore, when the aluminum compound is used in a fabrication process of an integrated circuit device, handling of the aluminum compound may be facilitated, and the aluminum compound may be suitable as a raw material for forming a thin film by ALD.

In an example embodiment, each of $R^1$ and $R^3$ may be a tertiary alkyl group. For example, the aluminum compound represented by General Formula (I) may be an aluminum compound represented by one of Chemical Formula (1) and Chemical Formula (2).

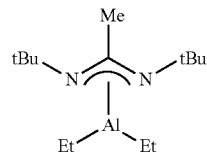

Chemical Formula (1)

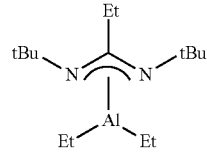

Chemical Formula (2)

As shown in Chemical Formula (1) and Chemical Formula (2), in the aluminum compound according to the present example embodiment, each of $R^1$ and $R^3$ may be a tertiary butyl group in order to minimize the number of β-H. In this case, since β-H is not present in the aluminum compound, deterioration of thermal stability of the aluminum compound due to β-H elimination may be prevented.

FIG. 1 is a flowchart of a method of forming a thin film according to an example embodiment.

Referring to FIG. 1, in a process P12, a substrate is prepared.

The substrate may have a configuration as described below as to a substrate 110 with reference to FIG. 3A.

In a process P14 of FIG. 1, an aluminum-containing film is formed on the substrate by using a raw material for forming a thin film, the raw material including an aluminum compound represented by General Formula (I).

In some embodiments, the aluminum compound included in the raw material used in the process P14 may be a liquid at room temperature.

In some embodiments, the aluminum compound used in the process P14 may have a thermal decomposition temperature of about 350° C. to about 500° C. In some embodiments, the aluminum compound may have one of structures represented by Chemical Formula (1) and Chemical Formula (2).

In the method of forming the thin film, according to an example embodiment, the raw material for forming a thin film may include at least one of aluminum compounds according to embodiments. The raw material for forming a thin film may vary with a thin film intended to be formed. In an embodiment, the raw material for forming a thin film may not include metal compounds and semimetal compounds other than the aluminum compound according to the present example embodiment. In another embodiment, when a thin film including two or more metals and/or semimetals is fabricated, the raw material for forming a thin film may include a compound (referred to by the term "another precursor" hereinafter) including a desired metal or semimetal, in addition to the aluminum compound according to the present example embodiment. In a further embodiment, the raw material for forming a thin film may include an organic solvent or a nucleophilic reagent in addition to the aluminum compound according to the present example embodiment.

Examples of the other precursor that may be used in the method of forming the thin film may include at least one Si or metal compound selected from among compounds having hydride, hydroxide, halide, azide, alkyl, alkenyl, cycloalkyl, allyl, alkynyl, amino, dialkylaminoalkyl, monoalkylamino, dialkylamino, diamino, di(silyl-alkyl)amino, di(alkyl-silyl) amino, disilylamino, alkoxy, alkoxyalkyl, hydrazide, phosphide, nitrile, dialkylaminoalkoxy, alkoxyalkyldialkylamino, siloxy, diketonate, cyclopentadienyl, silyl, pyrazolate, guanidinate, phosphoguanidinate, amidinate, phosphoamidinate, ketoiminate, diketoiminate, or carbonyl groups as ligands.

A metal included in the precursor may include Ti, Ta, Mg, Ca, Sr, Ba, Ra, Sc, Y, Zr, Hf, V, Nb, Cr, Mo, W, Mn, Fe, Os, Co, Rh, Ir, Ni, Pd, Pt Cu, Ag, Au, Zn, Cd, Ga, In, Ge, Sn, Pb, Sb, Bi, La, Ce, Pr, Nd, Pm, Sm, Eu, Gd, Tb, Dy, Ho, Er, Tm, Yb, or the like. However, the inventive concept is not limited to the metals set forth above as examples.

The raw material for forming a thin film, which includes the aluminum compound according to the present example embodiment, may be suitably used for an ALD process, and the aluminum compound according to the present example embodiment may be used as an Al precursor required for an ALD process in a process of forming a thin film, which is used for the fabrication of an integrated circuit device.

In the method of forming the thin film, according to embodiments, the aluminum-containing film may be formed in a reaction chamber of a deposition apparatus by using the aluminum compound represented by General Formula (I). For example, to form the aluminum-containing film, the aluminum compound may be supplied into the reaction chamber maintained at a temperature of about 300° C. to about 600° C. The reaction chamber may be maintained at a pressure of about 10 Pa to atmospheric pressure. In some embodiments, to form the aluminum-containing film, the aluminum compound may be supplied alone onto the substrate. In some other embodiments, to form the aluminum-containing film, a multi-component raw material, which includes a mixture of the aluminum compound and at least one of a precursor compound, a reactive gas, and an organic solvent, may be supplied onto the substrate, the precursor compound including a metal that is different from aluminum. The time for supplying the gases into the reaction chamber once may range from about 0.1 seconds to about 100 seconds.

In some embodiments, when an aluminum nitride film is formed, the reactive gas may be selected from among $NH_3$, a monoalkylamine, a dialkylamine, a trialkylamine, an organic amine compound, a hydrazine compound, or a combination thereof.

In some embodiments, when an aluminum oxide film is formed, the reactive gas may be an oxidative gas selected from among $O_2$, $O_3$, plasma $O_2$, $H_2O$, $NO_2$, NO, $N_2O$ (nitrous oxide), $CO_2$, $H_2O_2$, HCOOH, $CH_3COOH$, $(CH_3CO)_2O$, or a combination thereof.

In some further embodiments, the reactive gas may be a reductive gas, for example, $H_2$.

The aluminum compound and the reactive gas may be simultaneously or sequentially supplied onto the substrate.

In the method of forming the thin film, according to embodiments, the substrate for forming the thin film may include: a silicon substrate; a ceramic substrate such as SiN, TiN, TaN, TiO, RuO, ZrO, HfO, or LaO; a glass substrate; a metal substrate such as ruthenium, or the like.

Figure 2:
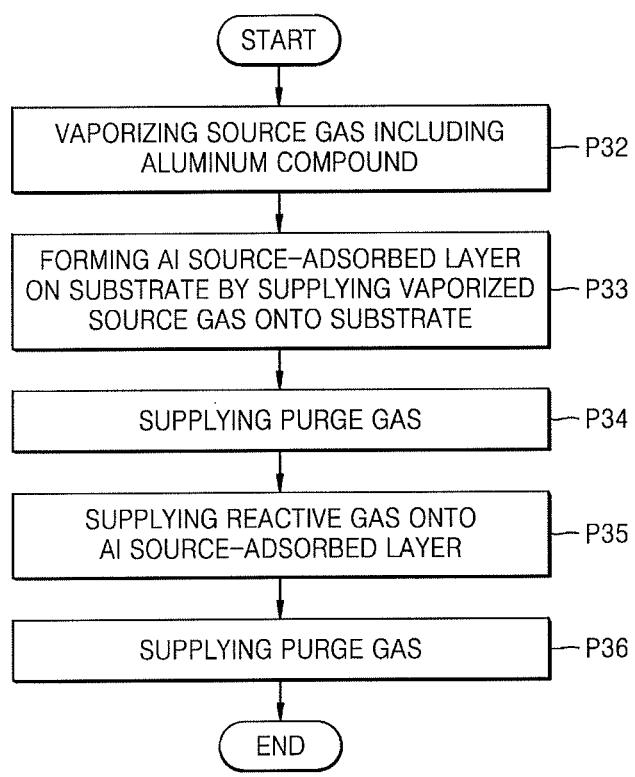
FIG. 2 illustrates a flow chart of an example method of forming an aluminum-containing film according to an example embodiment.

FIG. 2 is a flow chart of an example method of forming an aluminum-containing film, according to an example embodiment. The method of forming the aluminum-containing film by an ALD process, according to the process P14 of FIG. 1, will be described with reference to FIG. 2.

Referring to FIG. 2, in a process P32, a source gas including an aluminum compound is vaporized. The aluminum compound may include the aluminum compound represented by General Formula (I).

In a process P33, an Al source-adsorbed layer is formed on a substrate by supplying the vaporized source gas obtained according to the process P32 onto the substrate while maintaining an inside of a chamber at a temperature of about 300° C. to about 600° C. The Al source-adsorbed layer including a chemisorbed layer and a physisorbed layer of the source gas may be formed on the substrate by supplying the source gas onto the substrate.

In a process P34, undesired by-products on the substrate are removed by supplying a purge gas onto the substrate while maintaining the inside of the chamber at a temperature of about 300° C. to about 600° C. The purge gas may include, for example, an inert gas such as Ar, He, or Ne, $N_2$ gas, or the like.

In a process P35, a reactive gas is supplied onto the Al source-adsorbed layer formed on the substrate while maintaining the inside of the chamber at a temperature of about 300° C. to about 600° C.

In some embodiments, when an aluminum nitride film is formed, the reactive gas may be selected from among $NH_3$, a monoalkylamine, a dialkylamine, a trialkylamine, an organic amine compound, a hydrazine compound, or a combination thereof.

In some other embodiments, when an aluminum oxide film is formed, the reactive gas may be an oxidative gas selected from among $O_2$, $O_3$, plasma $O_2$, $H_2O$, $NO_2$, NO, $N_2O$, $CO_2$, $H_2O_2$, HCOOH, $CH_3COOH$, $(CH_3CO)_2O$, or a combination thereof.

In some further embodiments, the reactive gas may be a reductive gas, for example, $H_2$.

In a process P36, undesired by-products on the substrate are removed by supplying a purge gas onto the substrate.

After the process P36 is performed, a process of annealing the aluminum-containing film may be performed. The annealing may be performed at a temperature that is higher than the process temperature used in the processes P33 to P36. For example, the annealing may be performed at a temperature selected from a range of about 500° C. to about 1150° C. In some embodiments, the annealing may be performed in a nitrogen atmosphere. As described above, when the annealing process is performed, the aluminum-containing film may be densified and may exhibit improved film properties by removal of impurities in the aluminum-containing film. For example, when an aluminum oxide film is formed by the processes of FIG. 2, the aluminum oxide film may be shrunk due to densification thereof by the annealing process, and thus may have an increased density.

The method of forming the aluminum-containing film, which has been described with reference to FIG. 2, is merely an example, and various modifications and changes of the method may be made without departing from the spirit and scope of the embodiments.

To form the aluminum-containing film, as an example, the aluminum compound represented by General Formula (I), and at least one of another precursor, a reactive gas, a carrier gas, and a purge gas may be simultaneously or sequentially supplied onto the substrate.

According to an example embodiment, when the aluminum-containing film is formed by an ALD process, the number of ALD cycles may be adjusted in order to control the aluminum-containing film to a desired thickness.

For example, when the aluminum-containing film is formed by an ALD process, energy such as plasma, light, voltage, or the like may be applied. A time point for applying the energy may be variously selected. For example, at a time point at which the source gas including the aluminum compound is introduced into the reaction chamber, at a time point at which the source gas is adsorbed onto the substrate, at a time point at which an exhaust process is performed by using the purge gas, at a time point at which the reactive gas is introduced into the reaction chamber, or between these time points, the energy such as plasma, light, voltage, or the like may be applied.

The method of forming the thin film, according to the present example embodiment, may further include a process of annealing the aluminum-containing film in an inert, oxidative, or reductive atmosphere, after the aluminum-containing film is formed by using the aluminum compound represented by General Formula (I). In addition, to fill a step formed on a surface of the aluminum-containing film, the method of forming the thin film may further include a process of reflowing the aluminum-containing film, as needed. Each of the annealing process and the reflow process may be performed at a temperature selected from a range of about 200° C. to about 1150° C., without being limited thereto.

According to the method of forming the thin film, the aluminum compound according to the present example embodiment, the other precursor used together with the aluminum compound, the reactive gas, and the conditions for forming the thin film may be appropriately selected, thereby forming various aluminum-containing films.

In some embodiments, the aluminum-containing film formed by the method of forming the thin film, according to the present example embodiment, may include an aluminum oxide film represented by $Al_2O_3$, an aluminum nitride film represented by AlN, an aluminum alloy film, a composite oxide film including an aluminum alloy, or the like. In some embodiments, the composite oxide film may include a carbon atom. The carbon atom included in the composite oxide film may be derived from a carbon atom included in the aluminum compound represented by General Formula (I). Although the composite oxide film may include a composite oxide film of Ti and Al, a composite oxide film of Ta and Al, or the like, the inventive concept is not limited to the examples set forth above.

The aluminum-containing film fabricated by the method of forming the thin film, according to the present example embodiment, may be used for various purposes. For example, the aluminum-containing film may be used for a tunnel barrier of a gate insulating film included in a 3-dimensional charge trap flash (CTF) cell, a gate of a transistor, a conductive barrier film included in a metal wire such as a copper wire, a dielectric film of a capacitor, a barrier metal film for liquid crystals, a member for thin film solar cells, a member for semiconductor equipment, a nano-structure, or the like, without being limited thereto.

FIGS. 3A to 3H are cross-sectional views illustrating sequential processes of fabricating an integrated circuit device according to an example embodiment. A method of fabricating a memory cell array of an integrated circuit device 100 (see FIG. 3H) constituting a vertical non-volatile memory device will be described with reference to FIGS. 3A to 3H.

Figure 3A:
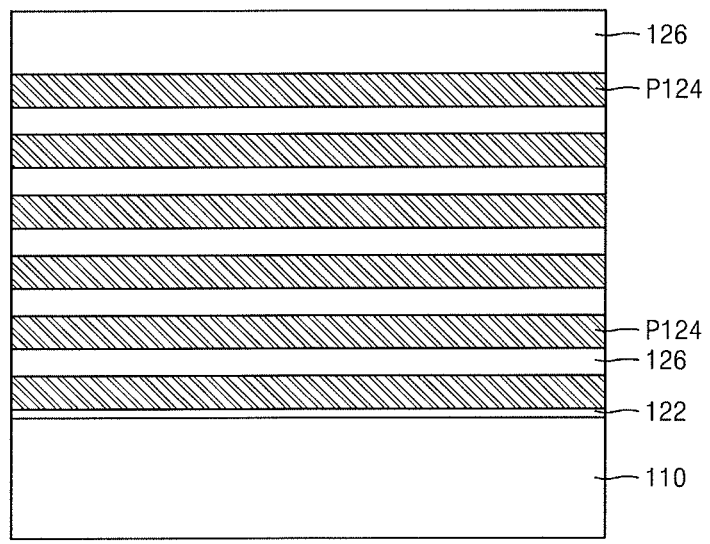
FIGS. 3A to 3H illustrate cross-sectional views illustrating sequential processes of fabricating an integrated circuit device according to an example embodiment.

Referring to FIG. 3A, an etch stop insulating film 122 is formed on a substrate 110, and a plurality of sacrificial layers P124 and a plurality of insulating layers 126 are alternately stacked on the etch stop insulating film 122, layer by layer. A thickness of an uppermost insulating layer 126 may be greater than a thickness of another insulating layer 126.

The substrate 110 may include a semiconductor such as Si or Ge, or a compound semiconductor such as SiC, GaAs, InAs, or InP. The substrate 110 may include a semiconductor substrate and structures including at least one insulating film or at least one conductive region on the semiconductor substrate. The at least one conductive region may include, for example, an impurity-doped well or an impurity-doped structure. In some embodiments, the substrate 110 may have various device isolation structures such as a shallow trench isolation (STI) structure.

The etch stop insulating film 122 and the plurality of insulating layers 126 may include an insulating material, for example, silicon oxide. The plurality of sacrificial layers P124 may include a material having an etch selectivity that is different from those of the etch stop insulating film 122 and the plurality of insulating layers 126. For example, the plurality of sacrificial layers P124 may include a silicon nitride film, a silicon oxynitride film, a polysilicon film, or a polysilicon germanium film.

Figure 3B:
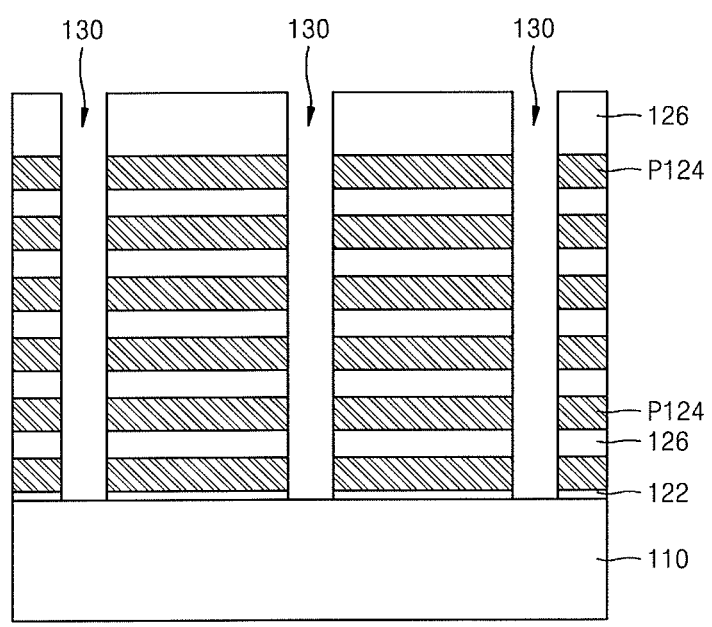

Referring to FIG. 3B, a plurality of channel holes 130 are formed, the plurality of channel holes 130 penetrating the plurality of insulating layers 126, the plurality of sacrificial layers P124, and the etch stop insulating film 122 and exposing the substrate 110.

Figure 3C:
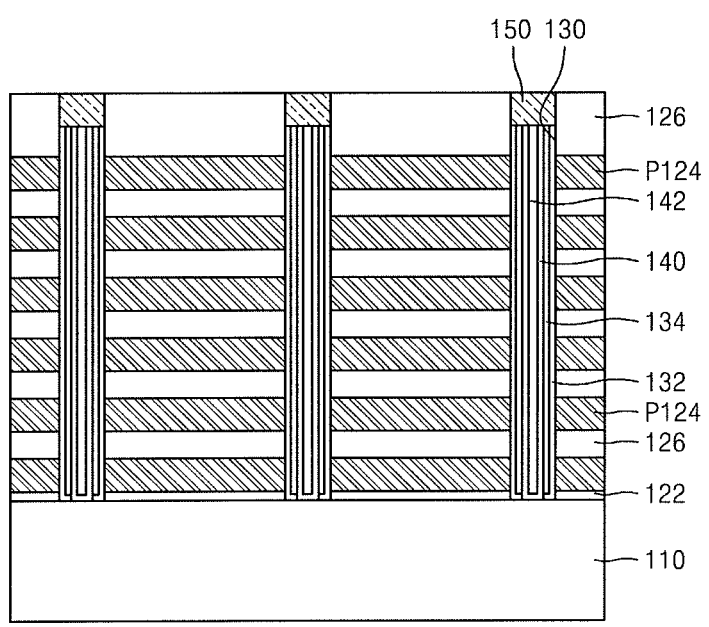

Referring to FIG. 3C, a charge storage film 132 and a tunnel dielectric film 134 are formed in this stated order and cover an inner wall of each of the plurality of channel holes 130, and a channel region 140 is formed and covers the tunnel dielectric film 134.

More specifically, the charge storage film 132 and the tunnel dielectric film 134 are formed in the plurality of channel holes 130. Next, a semiconductor layer for forming channel regions is formed on the tunnel dielectric film 134 in each of the plurality of channel holes 130, followed by anisotropically etching the semiconductor layer, thereby exposing the substrate 110 in each of the plurality of channel holes 130. The semiconductor layer may remain as the spacer-shaped channel region 140 covering a sidewall of the tunnel dielectric film 134 in each of the plurality of channel holes 130. In some embodiments, the charge storage film 132 may include a silicon nitride film. The tunnel dielectric film 134 may include a silicon oxide film.

The channel region 140 may not completely fill an inside of each channel hole 130. An insulating film 142 may fill a space remaining above the channel region 140 in each channel hole 130.

Next, the charge storage film 132, the tunnel dielectric film 134, the channel region 140, and the insulating film 142 in each of the plurality of channel holes 130 are partially removed, whereby an upper space is formed in each of the plurality of channel holes 130, and a conductive pattern 150 may fill the upper space. The conductive pattern 150 may include doped polysilicon or a metal. The conductive pattern 150 may be used as a drain region.

Figure 3D:
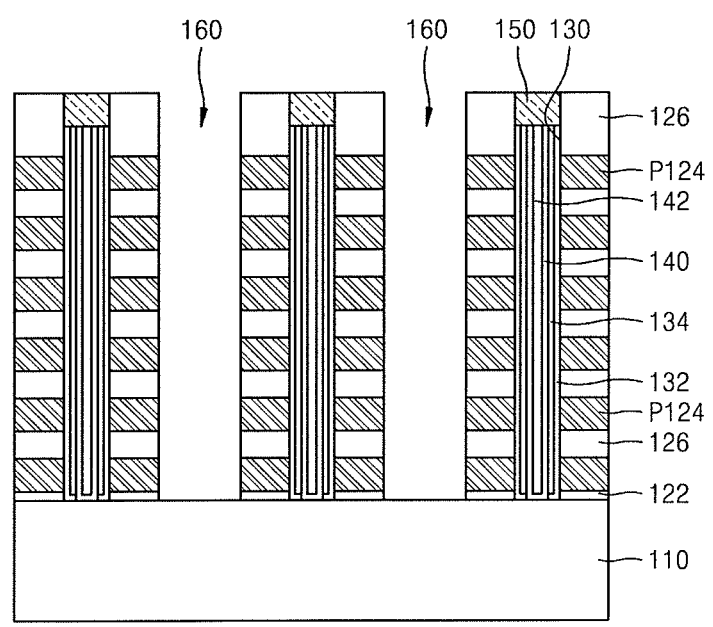

Referring to FIG. 3D, a plurality of openings 160 are formed, the plurality of openings 160 penetrating the plurality of insulating layers 126, the plurality of sacrificial layers P124, and the etch stop insulating film 122 and exposing the substrate 110.

Each of the plurality of openings 160 may be a word line cut region.

Figure 3E:
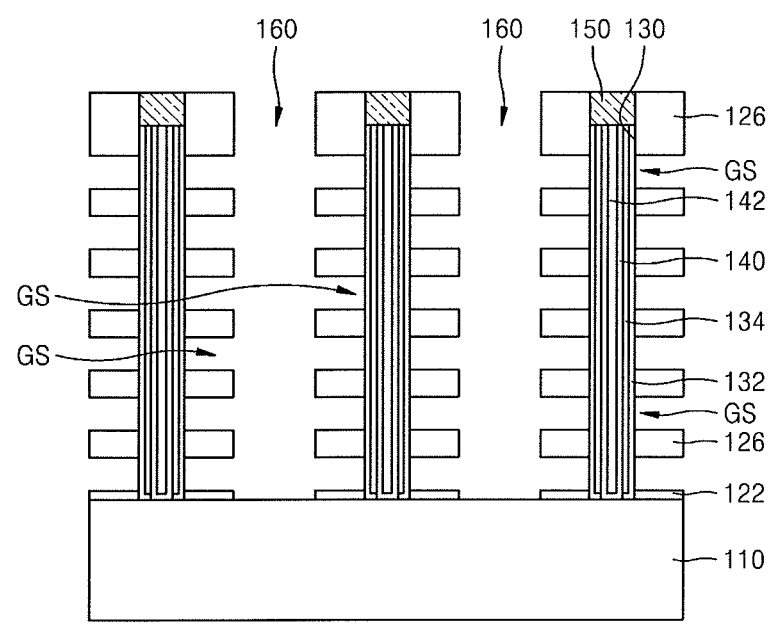

Referring to FIG. 3E, the plurality of sacrificial layers P124 are removed from the plurality of openings 160, thereby forming a plurality of gate spaces GS in such a manner that one gate space is arranged between two adjacent insulating layers of the plurality of insulating layers 126. The charge storage film 132 may be exposed by the plurality of gate spaces GS.

Figure 3F:
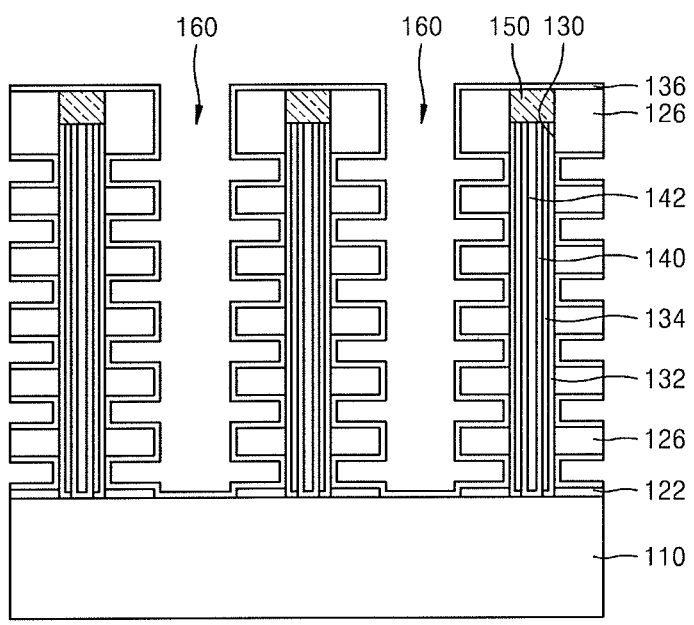

Referring to FIG. 3F, a blocking insulating film 136 is formed and covers inner walls of the plurality of gate spaces GS.

The blocking insulating film 136 may include an aluminum oxide film. To form the blocking insulating film 136, the method of forming the thin film may be used, the method having been described with reference to FIG. 1 or 2. In some embodiments, to form the blocking insulating film 136, an ALD process may be used. Here, as an Al source, the aluminum compound according to an example embodiment, for example, the aluminum compound represented by Chemical Formula (1) or (2), may be supplied through the plurality of openings 160. The ALD process may be performed at a first temperature selected from a range of about 300° C. to about 600° C. After the formation of the aluminum oxide film, the aluminum oxide film may be densified by annealing the aluminum oxide film at a second temperature that is higher than the first temperature. The second temperature may be selected from a range of about 500° C. to about 1150° C.

Figure 3G:
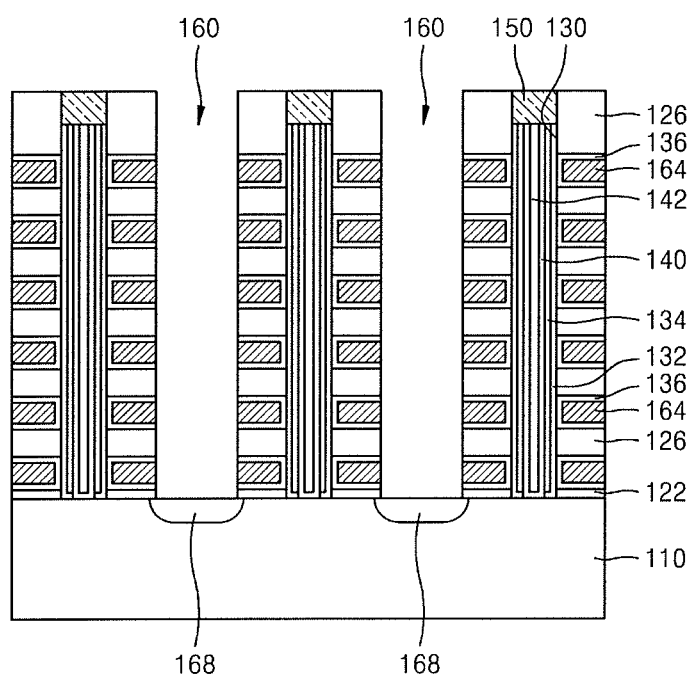

Referring to FIG. 3G, a conductive layer for gate electrodes is formed and fills spaces surrounded by the blocking insulating film 136 and remaining in the plurality of gate spaces GS, followed by partially removing the blocking insulating film 136 and the conductive layer for gate electrodes such that a sidewall of each of the plurality of insulating layers 126 in the plurality of openings 160 is exposed, whereby the blocking insulating film 136 and a gate electrode 164 remain in the plurality of openings 160.

In some embodiments, the gate electrode 164 may include a first conductive barrier film contacting the blocking insulating film 136, and a first conductive film on the first conductive barrier film. The first conductive barrier film may include a conductive metal nitride, for example, TiN or TaN. The first conductive film may include conductive polysilicon, a metal, a metal silicide, or a combination thereof.

The blocking insulating film 136 may include an aluminum oxide film free from undesired foreign substances such as carbon residues. As described with reference to FIG. 3F, the aluminum oxide film is annealed and thus densified, which may help prevent, for example. damage of a constitution material of the gate electrode 164 filling the gate spaces GS since an excess of the blocking insulating film 136 is consumed by an etching solution or the blocking insulating film 136 at entrance sides of the plurality of gate spaces GS is subjected to undesired removal by the etching solution, while the blocking insulating film 136 and the conductive layer for gate electrodes are partially removed in the process of FIG. 3G such that the sidewall of each of the plurality of insulating layers 126 is exposed.

As described above, after the formation of the blocking insulating film 136 and the gate electrode 164 in each of the plurality of gate spaces GS, the substrate 110 may be exposed by the plurality of openings 160. A plurality of common source regions 168 may be formed in the substrate 110 by implanting impurities into the substrate 110 exposed by the plurality of openings 160.

Figure 3H:
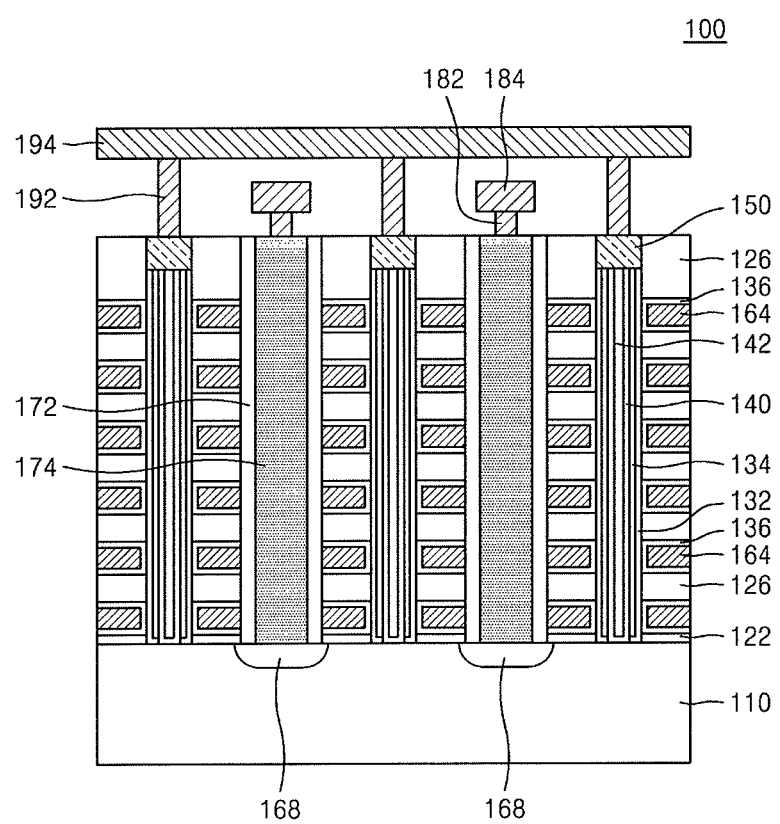

Referring to FIG. 3H, an insulating spacer 172 is formed on an inner sidewall of each of the plurality of openings 160, and a conductive plug 174 fills an inner space of each of the plurality of openings 160.

In some embodiments, the insulating spacer 172 may include a silicon oxide film, a silicon nitride film, or a combination thereof. The conductive plug 174 may include a second conductive barrier film contacting the insulating spacer 172, and a second conductive film filling a space surrounded by the second conductive barrier film in each of the plurality of openings 160. The second conductive barrier film may include a conductive metal nitride, for example, TiN or TaN. The second conductive film may include a metal, for example, tungsten.

A plurality of first contacts 182 may be formed on a plurality of conductive plugs 174, and a plurality of first conductive layers 184 may be formed on the plurality of first contacts 182. Each of the plurality of first contacts 182 and the plurality of first conductive layers 184 may include a metal, a metal nitride, or a combination thereof.

A plurality of second contacts 192 and a plurality of bit lines 194 may be formed on a plurality of conductive patterns 150. Each of the plurality of second contacts 192 and the plurality of bit lines 194 may include a metal, a metal nitride, or a combination thereof.

According to the method of fabricating the integrated circuit device 100, which has been described with reference to FIGS. 3A to 3H, the aluminum compound according to an example embodiment is used in the ALD process for forming the blocking insulating film 136 including aluminum oxide, which may provide properties useful as a raw material compound upon the ALD process, for example, high thermal stability, low melting point, high vapor pressure, transportability in a liquid state, ease of vaporization, and the like. Therefore, the blocking insulating film 136 may be easily formed by using the aluminum compound according to an example embodiment. In addition, the blocking insulating film 136 having uniform step coverage along the depths of holes having relatively high aspect ratios may be obtained.

FIGS. 4A to 4J are cross-sectional views illustrating sequential processes of fabricating an integrated circuit device 200 (see FIG. 4J) according to a process order, according to example embodiments.

Figure 4A:
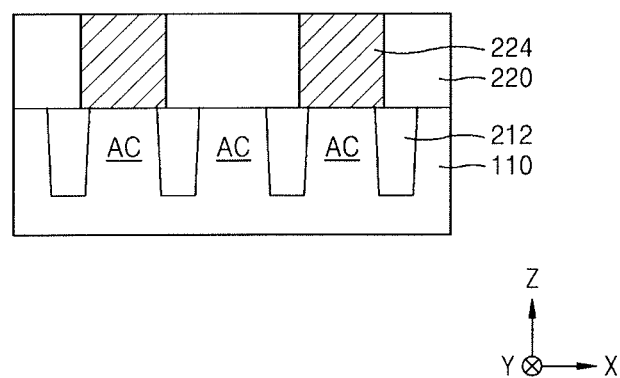
FIGS. 4A to 4J illustrate cross-sectional views illustrating sequential processes of fabricating an integrated circuit device according to example embodiments.

Referring to FIG. 4A, an interlayer dielectric 220 is formed on a substrate 110 including a plurality of active regions AC, followed by forming a plurality of conductive regions 224, which penetrate the interlayer dielectric 220 and are respectively connected to the plurality of active regions AC.

The plurality of active regions AC may be defined by a plurality of device isolation regions 212. The device isolation regions 212 may include a silicon oxide film, a silicon nitride film, a silicon oxynitride film, or a combination thereof. The interlayer dielectric 220 may include a silicon oxide film.

The plurality of conductive regions 224 may include polysilicon, a metal, a conductive metal nitride, a metal silicide, or a combination thereof.

Figure 4B:
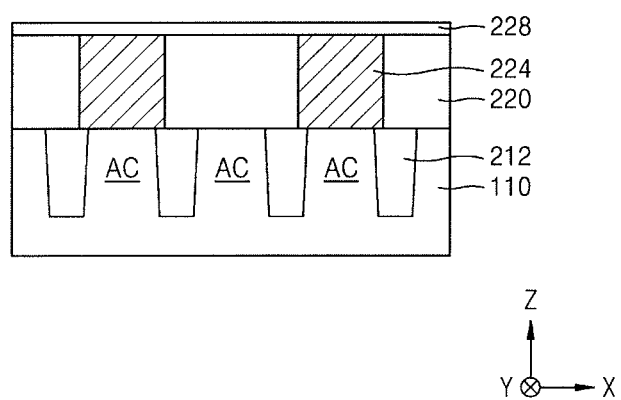

Referring to FIG. 4B, an insulating layer 228 is formed and covers the interlayer dielectric 220 and the plurality of conductive regions 224. The insulating layer 228 may be used as an etch stop layer.

The insulating layer 228 may include an insulating material having an etch selectivity with respect to the interlayer dielectric 220 and a mold film 230 (see FIG. 4C) that is formed in a subsequent process. In some embodiments, the insulating layer 228 may include silicon nitride, silicon oxynitride, or a combination thereof.

Figure 4C:
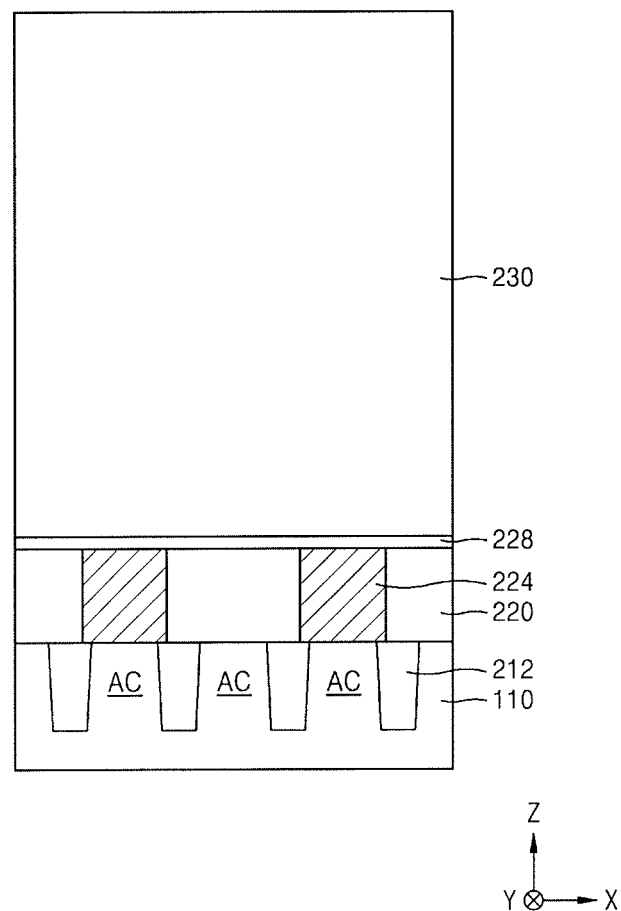

Referring to FIG. 4C, the mold film 230 is formed on the insulating layer 228. The mold film 230 may include an oxide film. In some embodiments, the mold film 230 may include a support film (not shown). The support film may include a material having an etch selectivity with respect to the mold film 230.

Figure 4D:
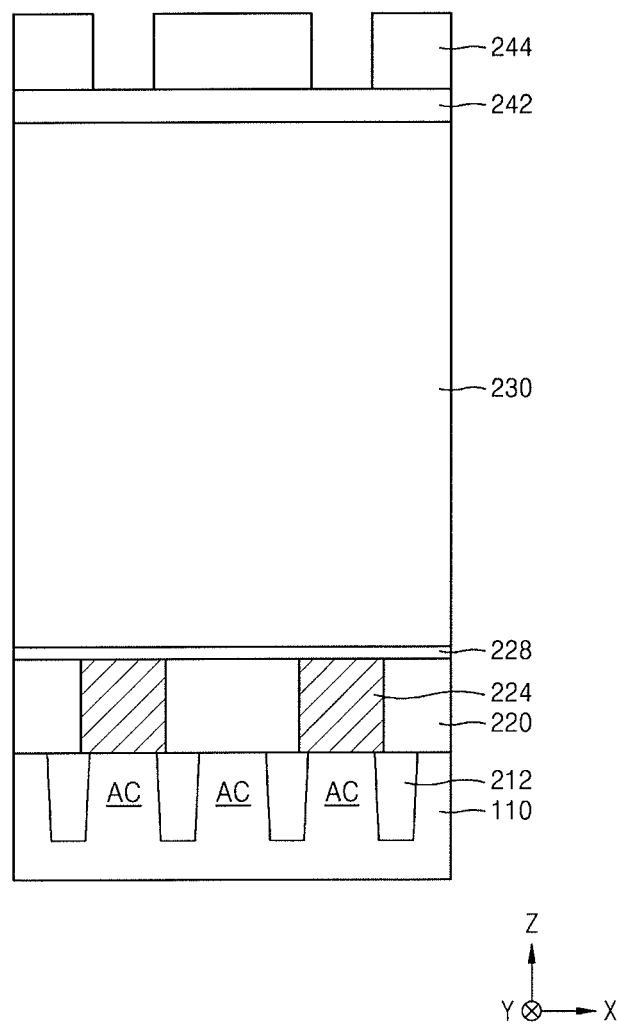

Referring to FIG. 4D, a sacrificial film 242 and a mask pattern 244 are formed on the mold film 230 in this stated order.

The sacrificial film 242 may include an oxide film. The sacrificial film 242 may protect the support film included in the mold film 230.

The mask pattern 244 may include an oxide film, a nitride film, a polysilicon film, a photoresist film, or a combination thereof. A region in which a lower electrode of a capacitor is to be formed may be defined by the mask pattern 244.

Figure 4E:
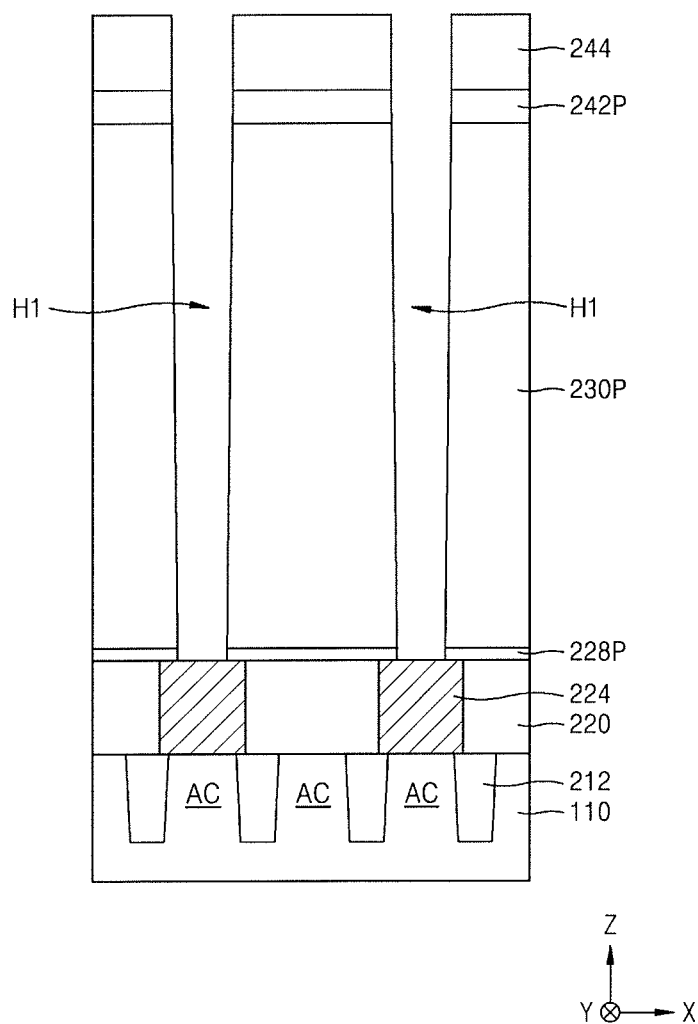

Referring to FIG. 4E, the sacrificial film 242 and the mold film 230 are dry-etched by using the mask pattern 244 as an etch mask and using the insulating layer 228 as an etch stop layer, thereby forming a sacrificial pattern 242P and a mold pattern 230P, which define a plurality of holes H1. Here, the insulating layer 228 may also be etched due to over-etch, whereby an insulating pattern 228P may be formed and expose the plurality of conductive regions 224.

Figure 4F:
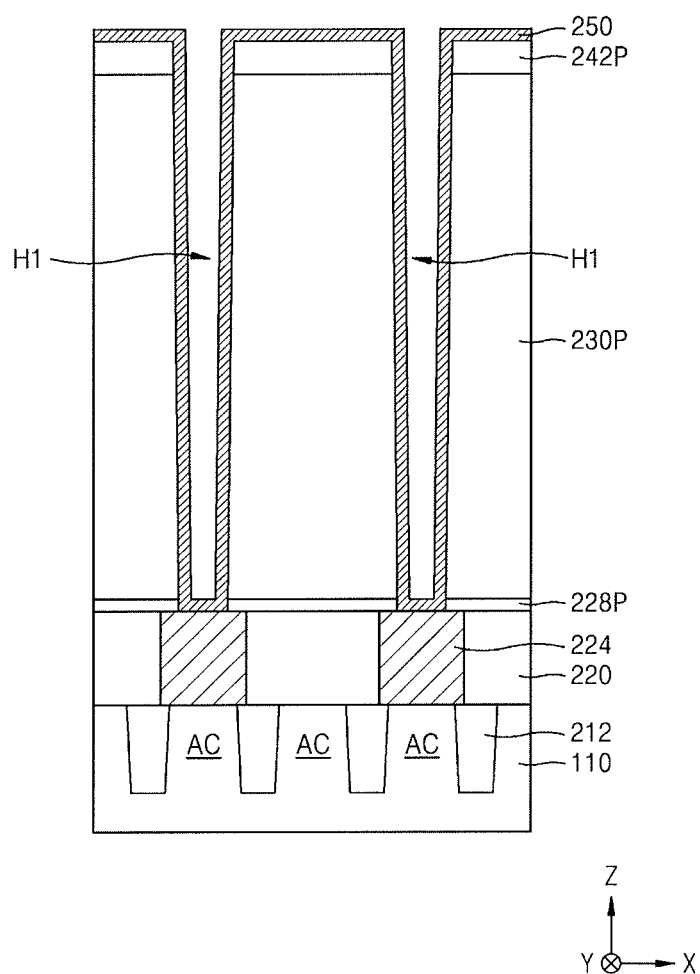

Referring to FIG. 4F, the mask pattern 244 is removed from the resultant of FIG. 4E, followed by forming a conductive film 250 for forming lower electrodes, the conductive film 250 covering an inner sidewall of each of the plurality of holes H1, an exposed surface of the insulating pattern 228P, an exposed surface of each of the plurality of conductive regions 224 inside the plurality of holes H1, and an exposed surface of the sacrificial pattern 242P.

The conductive film 250 for forming lower electrodes may be conformally formed on the sidewalls of the plurality of holes H1 such that an inner space of each of the plurality of holes H1 partially remains.

In some embodiments, the conductive film 250 for forming lower electrodes may include a doped semiconductor, a conductive metal nitride, a metal, a metal silicide, a conductive oxide, or a combination thereof. For example, the conductive film 250 for forming lower electrodes may include TiN, TiAlN, TaN, TaAlN, W, WN, Ru, $RuO_2$, $SrRuO_3$, Ir, $IrO_2$, Pt, PtO, SRO ($SrRuO_3$), BSRO (($Ba,Sr$)$RuO_3$), CRO ($CaRuO_3$), LSCO (($La,Sr$)$CoO_3$), or a combination thereof. To form the conductive film 250 for forming lower electrodes, a CVD, metal organic CVD (MOCVD), or ALD process may be used.

Figure 4G:
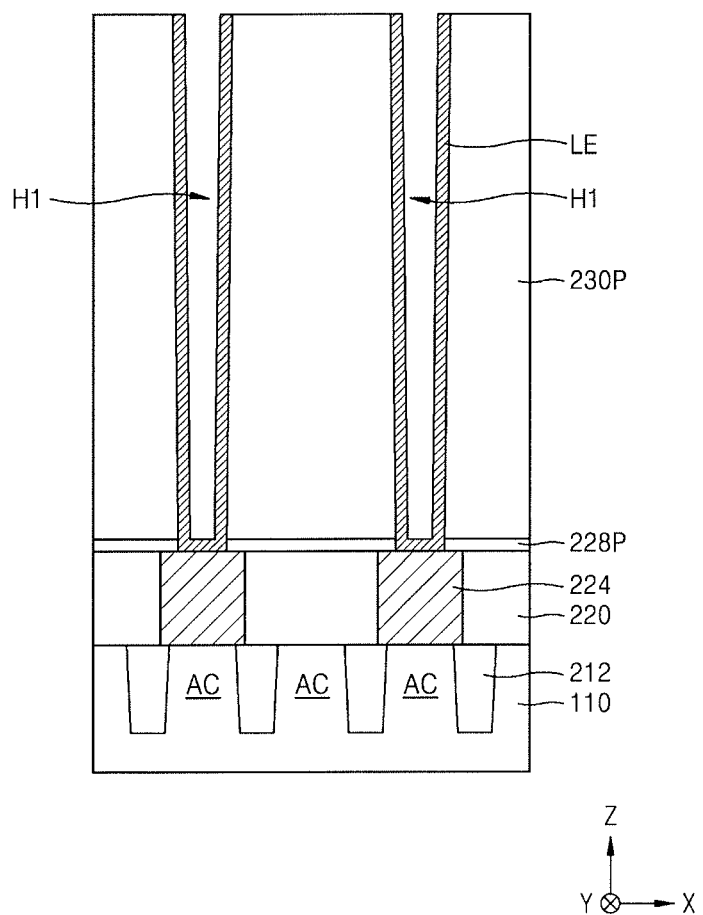

Referring to FIG. 4G, an upper side of the conductive film 250 for forming lower electrodes is partially removed, thereby dividing the conductive film 250 for forming lower electrodes into a plurality of lower electrodes LE.

To form the plurality of lower electrodes LE, a portion of the upper side of the conductive film 250 for forming lower electrodes and the sacrificial pattern 242P (see FIG. 4F) may be removed by using an etchback or chemical mechanical polishing (CMP) process such that an upper surface of the mold pattern 230P is exposed.

Figure 4H:
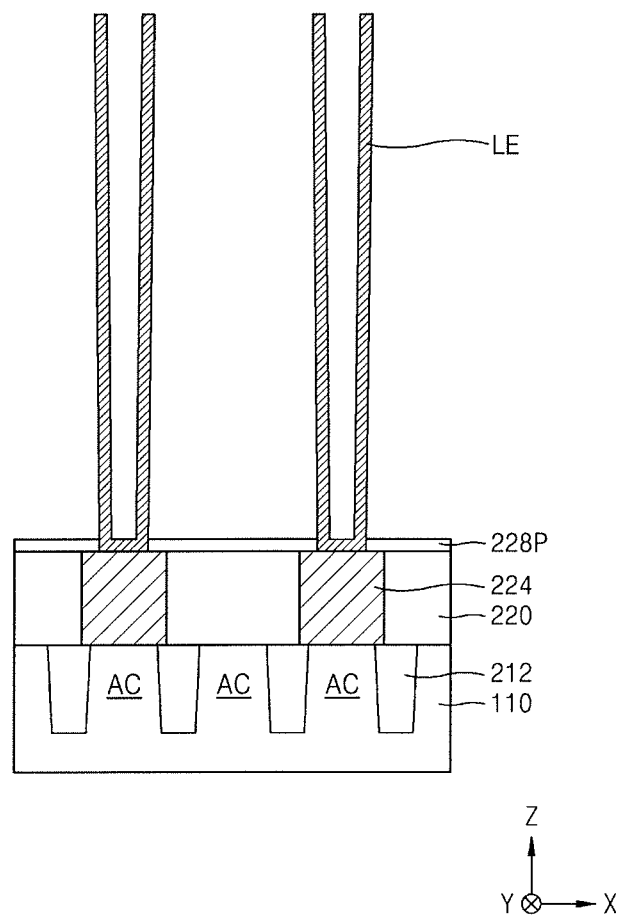

Referring to FIG. 4H, the mold pattern 230P is removed, thereby exposing outer walls of the plurality of lower electrodes LE having cylindrical shapes.

The mold pattern 230P may be removed by a lift-off process using LAL (ammonium fluoride, hydrofluoric acid, and water) or hydrofluoric acid.

Figure 4I:
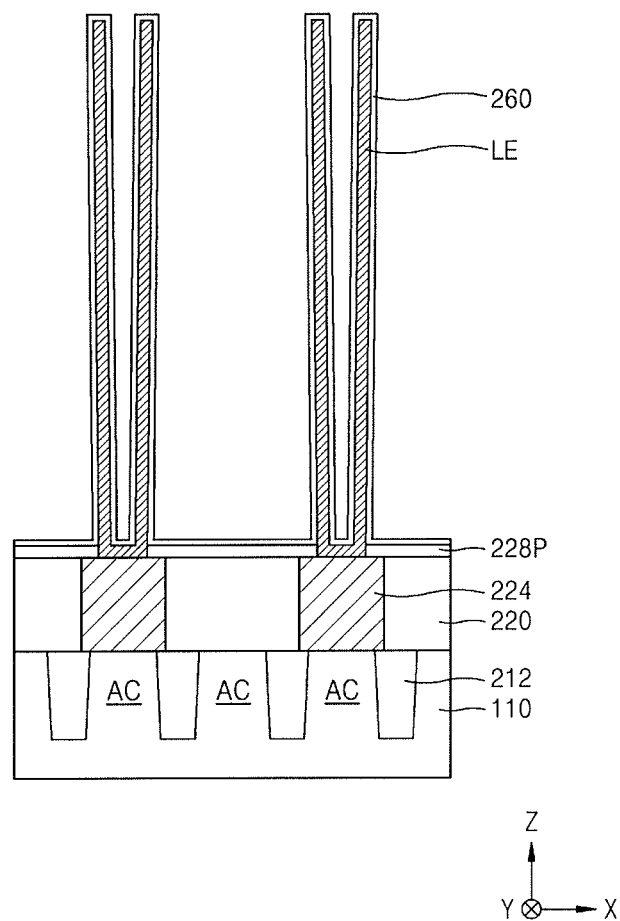

Referring to FIG. 4I, a dielectric film 260 is formed on the plurality of lower electrodes LE.

The dielectric film 260 may conformally cover exposed surfaces of the plurality of lower electrodes LE. The dielectric film 260 may include an aluminum oxide film. The dielectric film 260 may be formed by an ALD process. To form the dielectric film 260, the method of forming the thin film, according to the present example embodiment, may be used, the method having been described with reference to FIG. 1 or 2.

In some embodiments, the dielectric film 260 may include a single layer of an aluminum oxide film. In some other embodiments, the dielectric film 260 may include a combination of at least one aluminum oxide film and at least one high-K dielectric film selected from a tantalum oxide film and a zirconium oxide film.

In some embodiments, to form an aluminum oxide film constituting the dielectric film 260 by an ALD process, the aluminum compound according to the present example embodiment, for example, the aluminum compound represented by Chemical Formula (1) or (2), may be used as an Al source. The ALD process for forming the dielectric film 260 may be performed at about 300° C. to about 600° C. After the formation of the dielectric film 260, the dielectric film 260 may be annealed at a temperature of about 500° C. to about 1150° C.

Figure 4J:
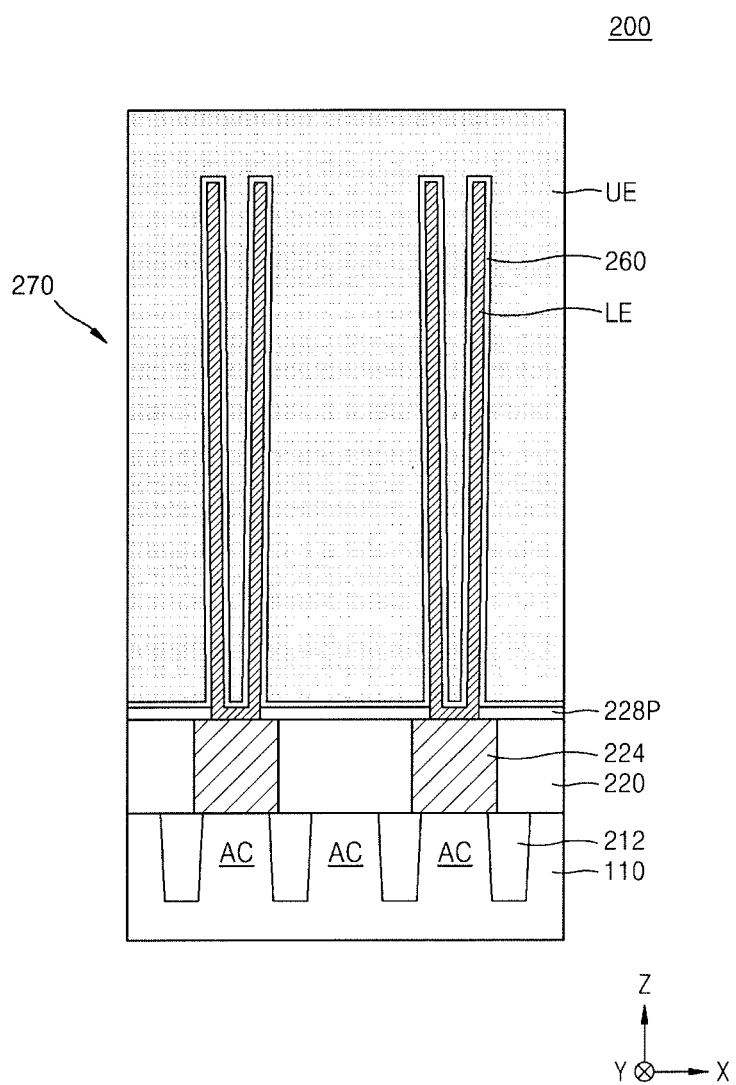

Referring to FIG. 4J, an upper electrode UE is formed on the dielectric film 260.

The lower electrode LE, the dielectric film 260, and the upper electrode UE may constitute a capacitor 270.

The upper electrode UE may include a doped semiconductor, a conductive metal nitride, a metal, a metal silicide, a conductive oxide, or a combination thereof. To form the upper electrode UE, a CVD, MOCVD, PVD, or ALD process may be used.

Although the method of fabricating the integrated circuit device 200, which includes the process of forming the dielectric film 260 of the capacitor 270, has been described with reference to FIGS. 4A to 4J, the inventive concept is not limited to the examples set forth above. For example, a pillar-type lower electrode having no inner space may be formed instead of the cylindrical lower electrode LE, and the dielectric film 260 may be formed on the pillar-type lower electrode.

The capacitor 270 of the integrated circuit device 200, which is formed by the method according to embodiments as described with reference to FIGS. 4A to 4J, includes the lower electrode LE having a 3-dimensional electrode structure in order to increase capacitance of the capacitor 270. To compensate reduction of capacitance due to reduction of a design rule, an aspect ratio of the 3-dimensional structured lower electrode LE is increasing. When the dielectric film 260 is formed on the lower electrode LE by an ALD process, the aluminum compound used for forming the dielectric film 260 may be easily delivered up to a lower portion of a 3-dimensional structure having a relatively high aspect ratio. Therefore, the dielectric film 260 exhibiting good step coverage may be formed on the lower electrode LE having a relatively high aspect ratio.

FIGS. 5A to 5D are cross-sectional views illustrating sequential processes of fabricating an integrated circuit device 300 (see FIG. 5D) according to a process order, according to example embodiments.

Figure 5A:
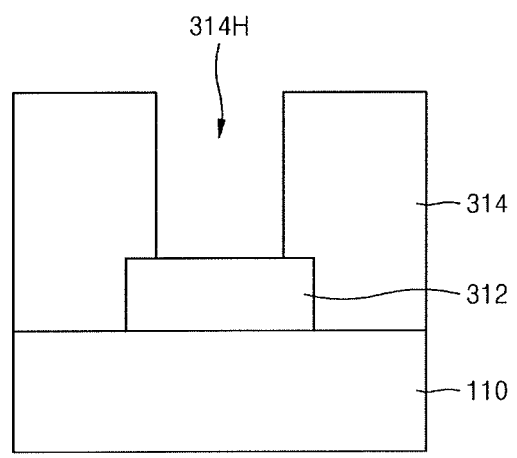
FIGS. 5A to 5D illustrate cross-sectional views illustrating sequential processes of fabricating an integrated circuit device according to example embodiments.

Referring to FIG. 5A, a conductive pattern 312 is formed on a substrate 110, and an interlayer dielectric pattern 314 having a hole 314H is formed on the conductive pattern 312. A portion of the conductive pattern 312 may be exposed by the hole 314H.

The conductive pattern 312 may be a source/drain region, a gate electrode, or a wiring layer. The interlayer dielectric pattern 314 may include a single layer or multiple layers. The interlayer dielectric pattern 314 may include a silicon oxide film, a silicon nitride film, or a combination thereof.

Figure 5B:
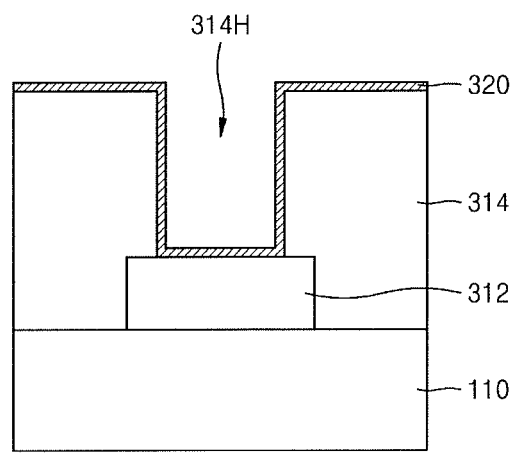

Referring to FIG. 5B, a conductive barrier film 320 is formed on an exposed surface of the conductive pattern 312 and an exposed surface of the interlayer dielectric pattern 314 and covers an inner wall of the hole 314H.

The conductive barrier film 320 may include an aluminum nitride film. To form the conductive barrier film 320, an ALD process may be used. To form the conductive barrier film 320, the method of forming the thin film, according to the present example embodiment, may be used, the method having been described with reference to FIG. 1 or 2. To form an aluminum nitride film constituting the conductive barrier film 320 by an ALD process, the aluminum compound according to the present example embodiment, for example, the aluminum compound represented by Chemical Formula (1) or (2), may be used as an Al source. The ALD process for forming the conductive barrier film 320 may be performed at about 300° C. to about 600° C. After the formation of the conductive barrier film 320, the conductive barrier film 320 may be annealed at a temperature of about 500° C. to about 1150° C.

Figure 5C:
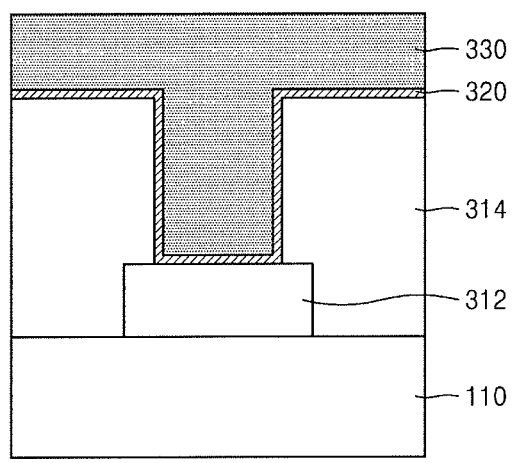

Referring to FIG. 5C, a wiring layer 330 is formed on the conductive barrier film 320, the wiring layer 330 having a sufficient thickness to fill the hole 314H (see FIG. 5B).

The wiring layer 330 may include a metal, for example, tungsten or copper.

Figure 5D:
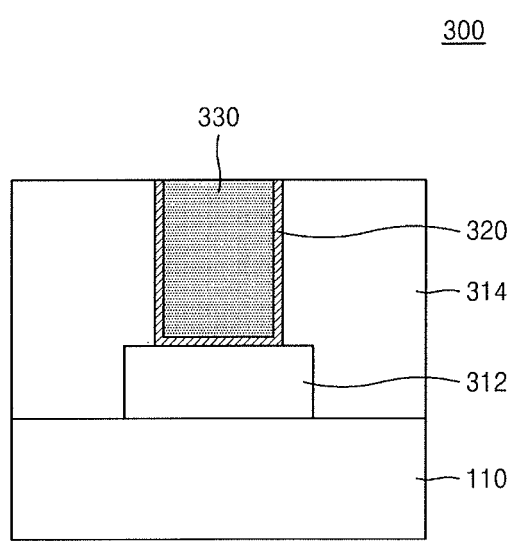

Referring to FIG. 5D, unnecessary portions of the conductive barrier film 320 and the wiring layer 330 are removed by using etchback, CMP, or a combination thereof, whereby the conductive barrier film 320 and the wiring layer 330 remain in the hole 314H (see FIG. 5B).

According to the method of fabricating the integrated circuit device 300, which has been described with reference to FIGS. 5A to 5D, the conductive barrier film 320 having an excellent film quality may be provided by significantly reducing amounts of impurities in the aluminum nitride film constituting the conductive barrier film 320, which may improve the reliability of the integrated circuit device 300.

Figure 6A:
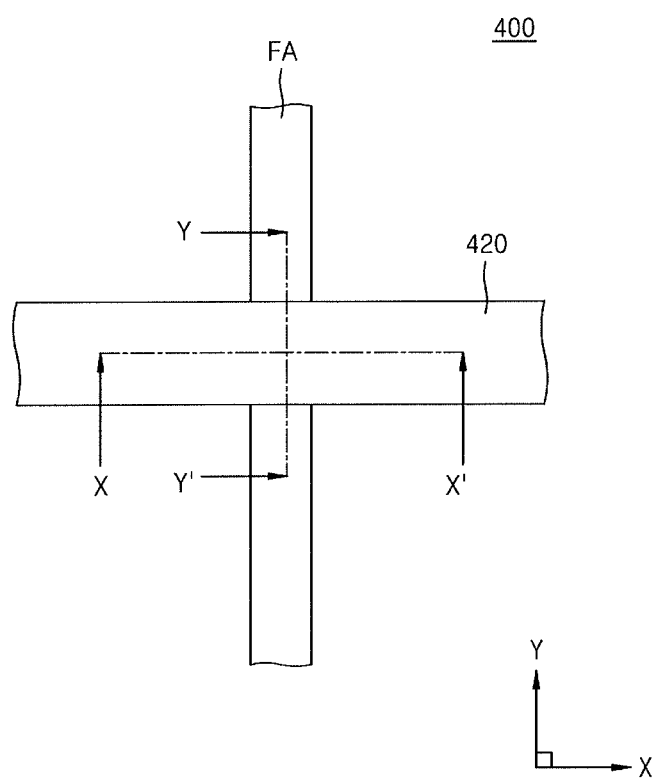
FIGS. 6A to 6C illustrate diagrams for explaining a method of fabricating an integrated circuit device, according to an example embodiment, and in particular.
Figure 6B:
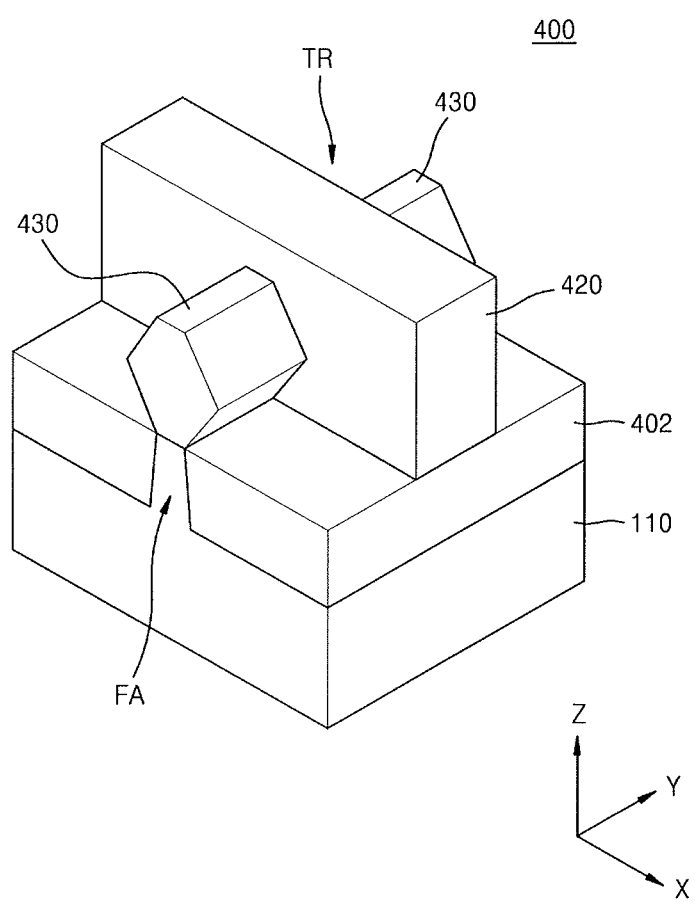
Figure 6C:
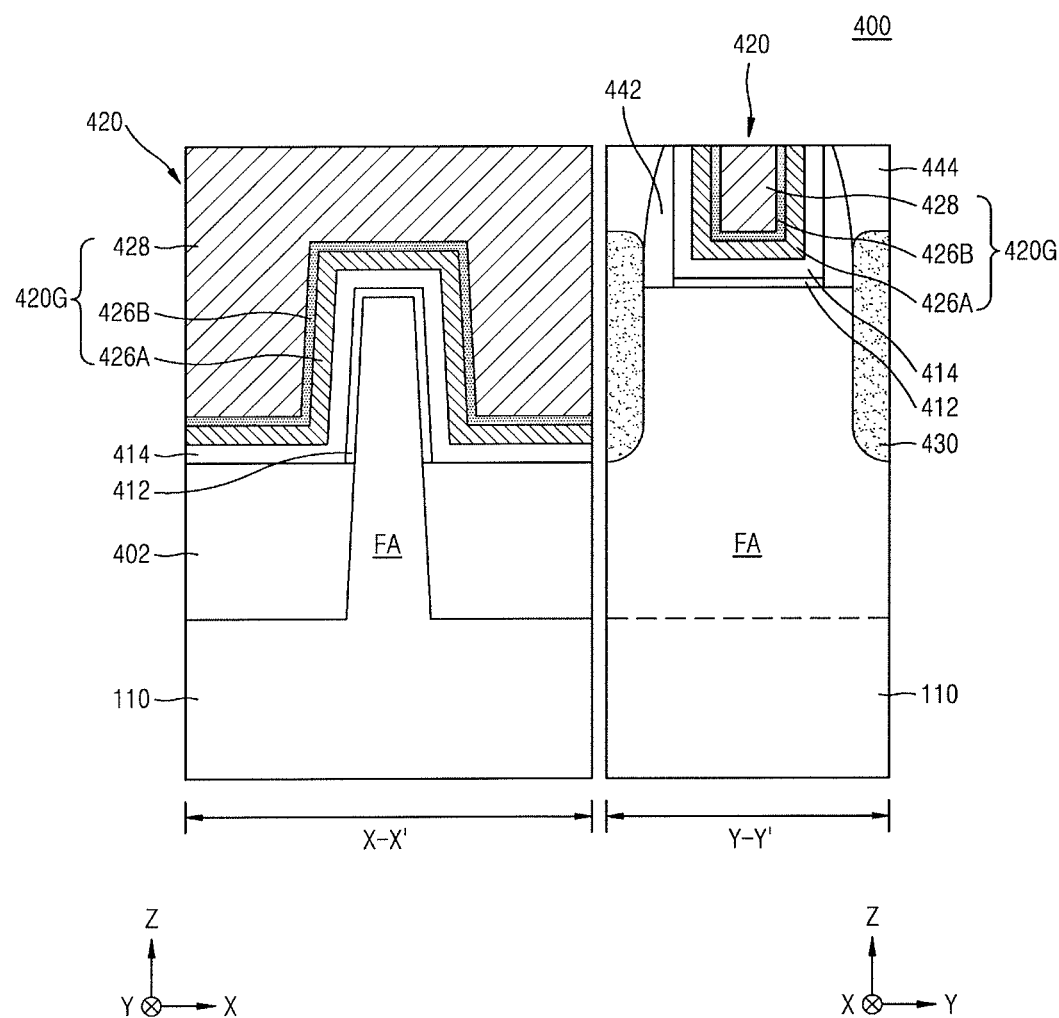

FIGS. 6A to 6C are diagrams for explaining a method of fabricating an integrated circuit device, according to an example embodiment, and in particular, FIG. 6A is a plan view of an integrated circuit device 400, FIG. 6B is a perspective view of the integrated circuit device 400 of FIG. 6A, and FIG. 6C shows cross-sectional views of the integrated circuit device 400, which are respectively taken along lines X-X' and Y-Y' of FIG. 6A.

Referring to FIGS. 6A to 6C, the integrated circuit device 400 includes a fin-type active region FA protruding from a substrate 110.

The fin-type active region FA may extend along one direction (Y direction in FIGS. 6A and 6B). A device isolation film 402 is formed on the substrate 110 and covers a lower sidewall of the fin-type active region FA. The fin-type active region FA protrudes in a fin shape upwards from the device isolation film 402. In some embodiments, the device isolation film 402 may include a silicon oxide film, a silicon nitride film, a silicon oxynitride film, or a combination thereof, without being limited thereto.

On the fin-type active region FA on the substrate 110, a gate structure 420 may extend in a direction (X direction) intersecting with the extension direction of the fin-type active region FA. A pair of source/drain regions 430 may be formed in the fin-type active region FA at both sides of the gate structure 420.

The pair of source/drain regions 430 may include a semiconductor layer epitaxially grown on the fin-type active region FA. Each of the pair of source/drain regions 430 may include an embedded SiGe structure including a plurality of epitaxially grown SiGe layers, an epitaxially grown Si layer, or an epitaxially grown SiC layer. The pair of source/drain regions 430 are not limited to an example shape shown in FIG. 6B, and may have various shapes.

A MOS transistor TR may be formed in a region in which the fin-type active region FA intersects with the gate structure 420. The MOS transistor TR may include a 3-dimensional structured MOS transistor in which channels are formed on an upper surface and both side surfaces of the fin-type active region FA. The MOS transistor TR may constitute an NMOS transistor or a PMOS transistor.

As shown in FIG. 6C, the gate structure 420 may include an interfacial layer 412, a high-K dielectric film 414, a first metal-containing layer 426A, a second metal-containing layer 426B, and a gap-fill metal layer 428, which are formed on a surface of the fin-type active region FA in this stated order. The first metal-containing layer 426A, the second metal-containing layer 426B, and the gap-fill metal layer 428 of the gate structure 420 may constitute a gate electrode 420G.

An insulating spacer 442 may be formed on both side surfaces of the gate structure 420. The insulating spacer 442 is covered with an interlayer dielectric 444.

The interfacial layer 412 may be formed on a surface of the fin-type active region FA. The interfacial layer 412 may include an insulating material such as an oxide film, a nitride film, or an oxynitride film.

The high-K dielectric film 414 may include a material having a greater dielectric constant than a silicon oxide film. For example, the high-K dielectric film 414 may have a dielectric constant of about 10 to about 25. The high-K dielectric film 414 may include a metal oxide or a metal oxynitride.

In some embodiments, the first metal-containing layer 426A may include a P-type work function conductive material, for example, TiN. The second metal-containing layer 426B may include an N-type work function conductive material, for example, an N-type metal-containing layer that is required for an NMOS transistor including an Al compound containing Ti or Ta. In some embodiments, the second metal-containing layer 426B may include an Al-containing film including a carbon atom. For example, the second metal-containing layer 426B may include TiAlC, TiAlCN, TaAlC, TaAlCN, or a combination thereof. In some other embodiments, the second metal-containing layer 426B may include TiAl, TiAlN, TaAlN, or a combination thereof.

To form the second metal-containing layer 426B, the method of forming the thin film may be used, the method having been described with reference to FIG. 1 or 2. To form the second metal-containing layer 426B, an ALD process may be used. Here, the aluminum compound according to an example embodiment, for example, the aluminum compound represented by Chemical Formula (1) or (2), may be used as an Al source. The ALD process for forming the second metal-containing layer 426B may be performed at about 300° C. to about 600° C. In some embodiments, after the formation of the second metal-containing layer 426B, the second metal-containing layer 426B may be annealed. The annealing may be performed at about 500° C. to about 1150° C.

The second metal-containing layer 426B may adjust a work function of the gate structure 420 in conjunction with the first metal-containing layer 426A. A threshold voltage of the gate structure 420 may be adjusted by work function adjustment of the first metal-containing layer 426A and the second metal-containing layer 426B.

The gap-fill metal layer 428 may fill a remaining gate space above the second metal-containing layer 426B when the gate structure 420 is formed by a replacement metal gate (RMG) process. If the remaining gate space above the second metal-containing layer 426B is not present after the formation of the second metal-containing layer 426B, the gap-fill metal layer 428 may be omitted instead of being formed on the second metal-containing layer 426B. The gap-fill metal layer 428 may include W, a metal nitride such as TiN or TaN, Al, a metal carbide, a metal silicide, a metal aluminum carbide, a metal aluminum nitride, or a metal silicon nitride.

When the integrated circuit device 400 is fabricated by the method according to embodiments, which has been described with reference to FIGS. 6A to 6C, an ALD process using the aluminum compound according to an example embodiment is performed to form the second metal-containing layer 426B, thereby improving the reliability of the integrated circuit device 400.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE 1

Synthesis of Compound Represented by Chemical Formula (1)

100 mL of a solution of methyllithium in ether (1.08 M, 29.7 mmol) was placed in a reaction flask in an argon atmosphere, and the reaction flask was cooled and maintained at a temperature of 0° C. to 6° C. While 4.5 g (29.2 mmol) of di-tert-butyl carbodiimide was slowly added dropwise into the reaction flask, the components were stirred for 1 hour. Next, 3.5 g (29.0 mmol) of diethylaluminum chloride was slowly added dropwise into the reaction flask, and the components were stirred for 15 minutes, thereby obtaining a resulting product in a liquid state. The obtained resulting product was filtered with a filter (Celite filter), followed by purifying the resulting product at a reduced pressure of 133.3 Pa, thereby obtaining 6.29 g of (di-tert-butyl(methyl) amidinate)diethyl aluminum in a colorless liquid state (yield 85%).

(Analysis)
$^1$H-NMR (C6D6, δ (ppm))
0.35 (4H, q), 1.10 (18H, s), 1.41 (6H, t), 1.70 (3H, s)

Figure 7:
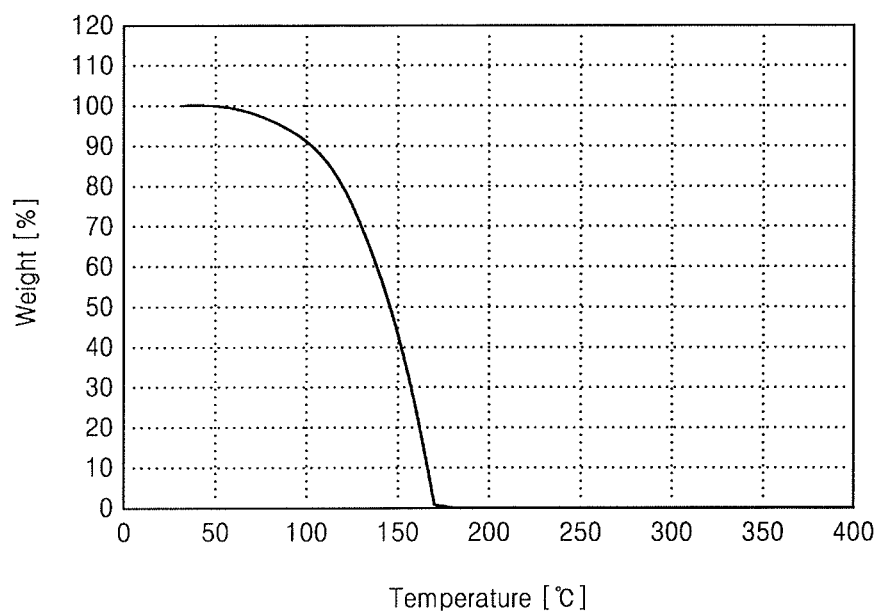
FIG. 7 illustrates a graph depicting results of thermogravimetric analysis (TGA) of an aluminum compound according to an example embodiment.

FIG. 7 is a graph depicting results of thermogravimetric analysis (TGA) of 10 mg of the compound represented by Chemical Formula (1) and obtained in Example 1 in an argon atmosphere under the condition of a heating rate of 10° C./min, the compound being obtained in Example 1.

FIG. 7 shows weight loss percentage along with temperature of the compound represented by Chemical Formula (1). As can be seen from FIG. 7, the compound represented by Chemical Formula (1) exhibited quick vaporization and was vaporized by 99% or more at about 170° C. without residues due to thermal decomposition.

Figure 8:
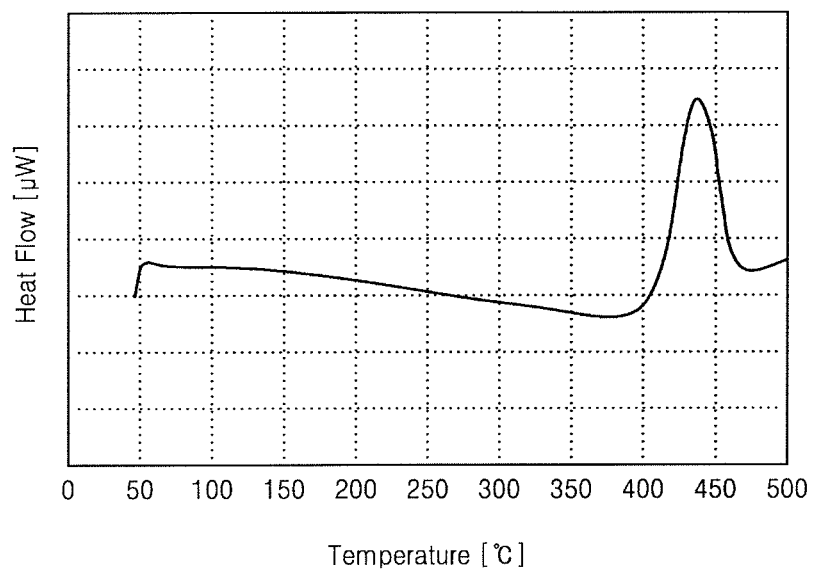
FIG. 8 illustrates a graph depicting results of differential scanning calorimetry (DSC) analysis of the aluminum compound according to an example embodiment.

FIG. 8 is a graph depicting results of differential scanning calorimetry (DSC) analysis of the compound represented by Chemical Formula (1) and obtained in Example 1.

For the evaluation of FIG. 8, 2 mg of the compound represented by Chemical Formula (1) was heated to 500° C. at a heating rate of 10° C./min. Here, a thermal decomposition peak was not observed up to 400° C.

Figure 9:
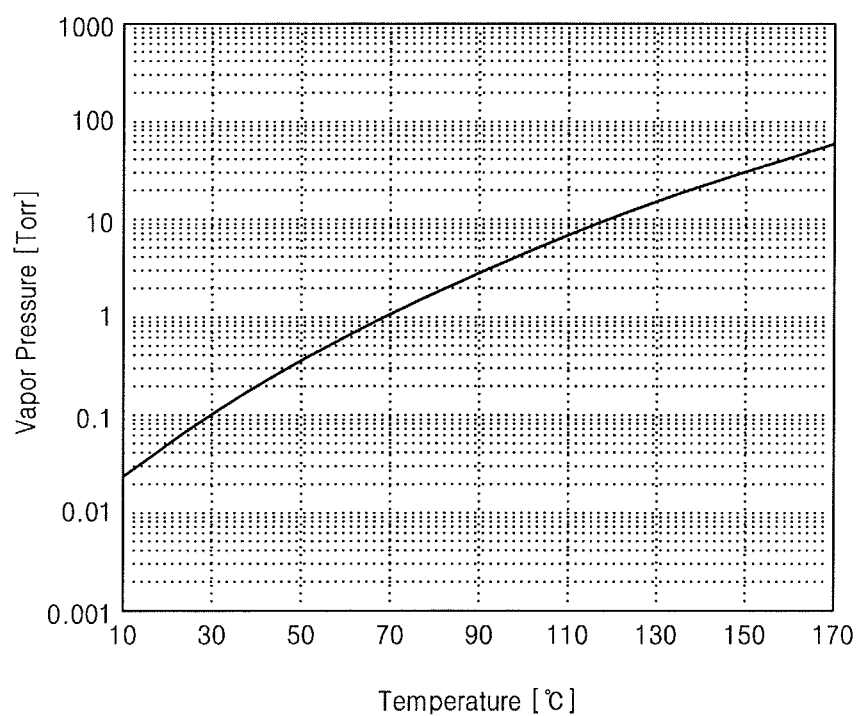
FIG. 9 illustrates a graph depicting measurement results of vapor pressure along with temperature for the aluminum compound according to an example embodiment.

FIG. 9 is a graph depicting measurement results of vapor pressure along with temperature for the compound represented by Chemical Formula (1) and obtained in Example 1.

From the results of FIG. 9, it was confirmed that the compound represented by Chemical Formula (1) had a vapor pressure of about 1 Torr at 70° C.

EXAMPLE 2

Synthesis of Compound Represented by Chemical Formula (2)

2.00 g (17.5 mmol) of a triethyl aluminum complex and 50 mL of an organic solvent (hexane) were placed in a reaction flask in an argon atmosphere, and the reaction flask was cooled and maintained at a temperature of 0° C. to 6° C. While 2.73 g (17.5 mmol) of di-tert-butyl carbodiimide was slowly added dropwise into the reaction flask, the components were stirred for 15 hours. An obtained resulting product was purified at a reduced pressure of 133.3 Pa, thereby obtaining 4.43 g of (di-tert-butyl(ethyl)amidinate) diethyl aluminum that was a colorless liquid (yield 94%).

(Analysis)

$^1$H-NMR (C6D6, δ (ppm))

0.35 (41-1, q), 0.98 (3H, t), 1.14 (1814, s), 1.40 (6H, t), 2.14 (2H, q)

Figure 10:
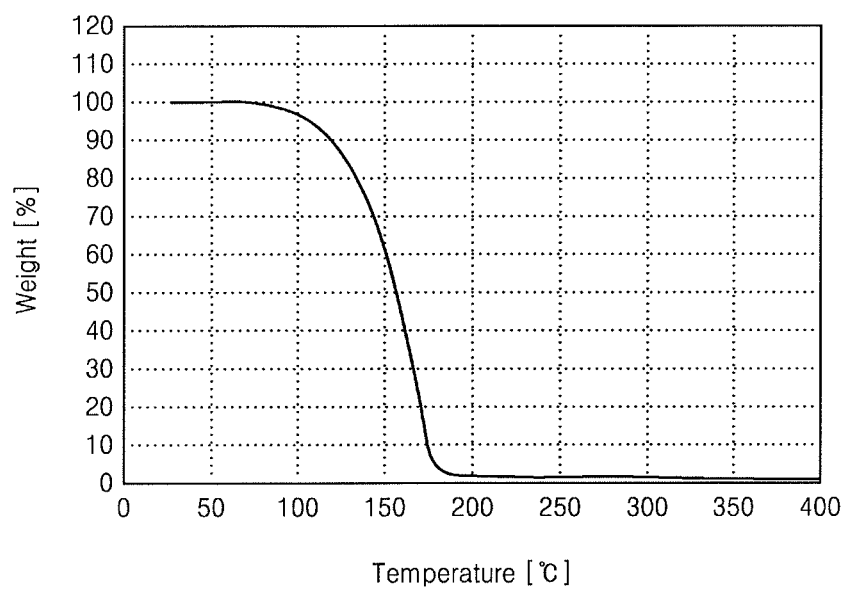
FIG. 10 illustrates a TGA graph of an aluminum compound according to an example embodiment.

FIG. 10 is a graph depicting results of TGA of 10 mg of the compound represented by Chemical Formula (2) and obtained in Example 2 in an argon atmosphere under the condition of a heating rate of 10° C./min.

As can be seen from FIG. 10, the compound represented by Chemical Formula (2) exhibited quick vaporization and was vaporized by 99% or more at about 170° C. without residues due to thermal decomposition.

Figure 11:
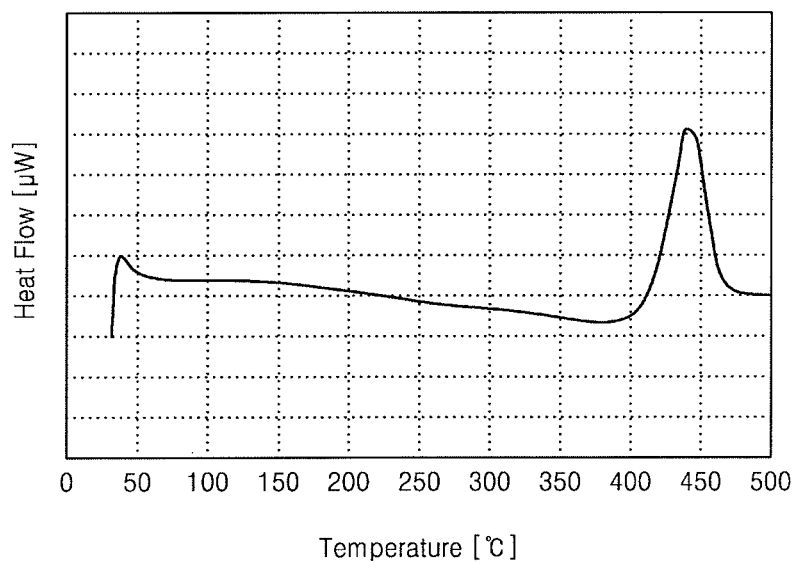
FIG. 11 illustrates a DSC analysis graph of the aluminum compound according to an example embodiment.

FIG. 11 is a graph depicting results of DSC analysis of the compound represented by Chemical Formula (2) and obtained in Example 2.

For the evaluation of FIG. 11, 2 mg of the compound represented by Chemical Formula (2) was heated to 500° C. at a heating rate of 10° C./min. Here, a thermal decomposition peak was not observed up to 400° C.

Figure 12:
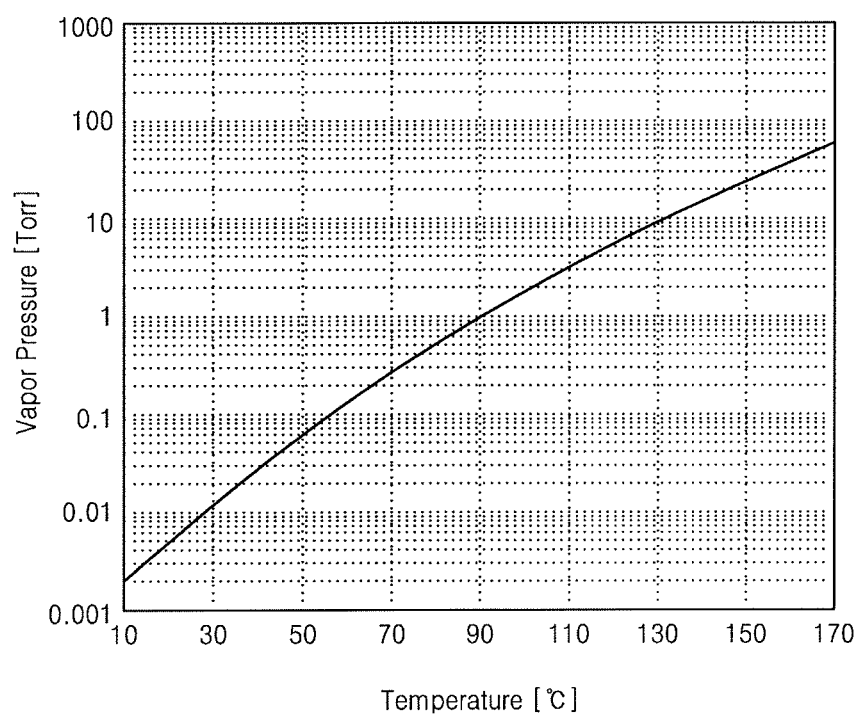
FIG. 12 illustrates a graph depicting measurement results of vapor pressure along with temperature for the aluminum compound according to an example embodiment.

FIG. 12 is a graph depicting measurement results of vapor pressure along with temperature for the compound represented by Chemical Formula (2) and obtained in Example 2.

From the results of FIG. 12, it was confirmed that the compound represented by Chemical Formula (2) had a vapor pressure of about 1 Torr at 70° C.

EXAMPLE 3

Formation of aluminum oxide film

An aluminum oxide film was formed on a silicon substrate by an ALD process by using each of the aluminum compounds represented by Chemical Formulae (1) and (2) as a raw material, the aluminum compounds being synthesized in Examples 1 and 2. Conditions of the ALD process for forming the aluminum oxide film were as follows.

Reaction temperature (substrate temperature): 200° C. to 500° C.

Reactive gas: H$_2$O (water gas)

(Process)

Under the above conditions, when the following series of processes (1) to (4) was defined as 1 cycle, 500 cycles were repeated.

Process (1): A process of performing deposition at a pressure of 2 hPa for 0.1 seconds to 1 second by introducing vapor of each of the aluminum compounds into the reaction chamber, the vapor being obtained by vaporizing each of the aluminum compounds under the conditions of a raw material container heating temperature of 70° C. and a raw material container pressure of 100 Pa.

Process (2): A process of removing the unreacted raw material by performing Ar purge for 4 seconds.

Process (3): A process of performing reaction at a pressure of 2 hPa for 0.1 seconds by introducing the reactive gas into the reaction chamber.

Process (4): A process of removing the unreacted raw material by performing Ar purge for 5 seconds.

Figure 13:
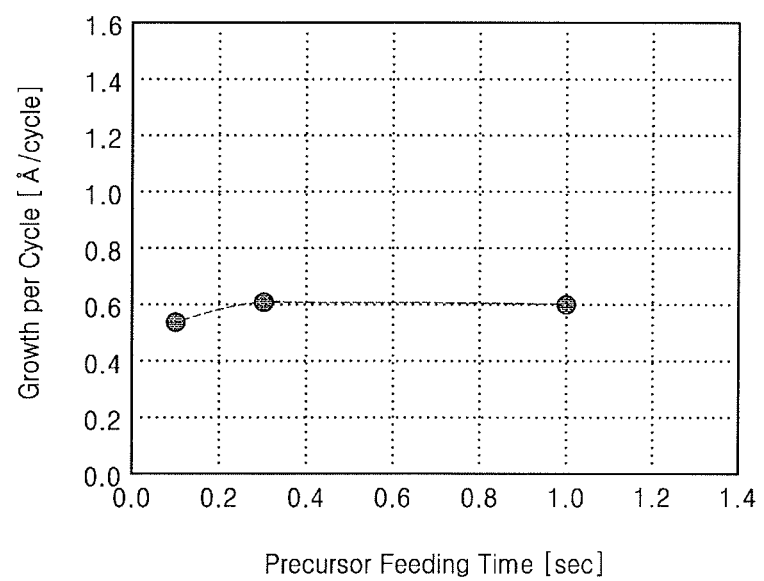
FIG. 13 illustrates a graph depicting measurement results of deposition rate along with precursor supply time for an aluminum oxide film formed by using an aluminum compound according to an example embodiment as a precursor.

FIG. 13 is a graph depicting measurement results of deposition rate along with precursor supply time for the aluminum oxide film formed at a substrate temperature of 500° C. by using the aluminum compound represented by Chemical Formula (1) as a precursor, in Example 3.

For the evaluation of FIG. 13, the deposition rate along with time for supplying the aluminum compound represented by Chemical Formula (1) into the reaction chamber was evaluated. As a result, the aluminum compound represented by Chemical Formula (1) showed an ideal ALD behavior allowing the ALD deposition rate to be constant after a thin film growth rate was saturated at a time point of about 0.3 seconds.

Figure 14:
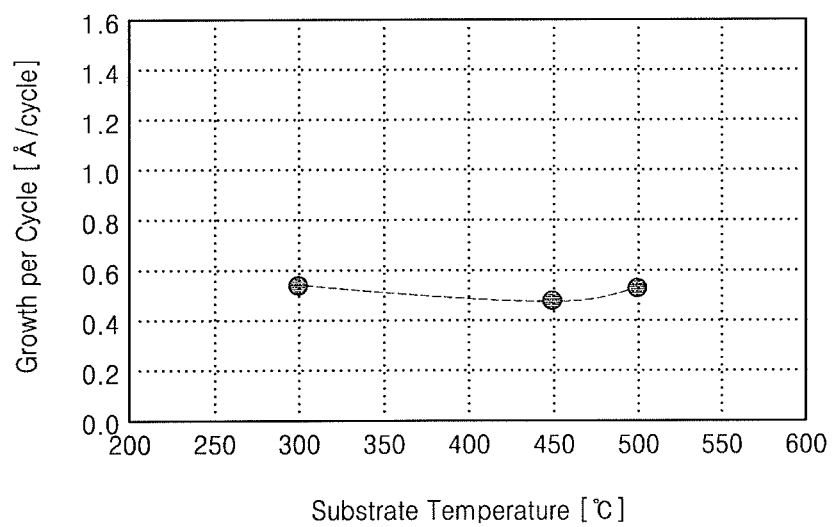
FIG. 14 illustrates a graph depicting measurement results of deposition rate along with process temperature for the aluminum oxide film formed by using the aluminum compound according to an example embodiment as a precursor.

FIG. 14 is a graph depicting measurement results of deposition rate along with process temperature for the aluminum oxide film formed by using the aluminum compound represented by Chemical Formula (1) as a precursor, in Example 3.

As can be seen from FIG. 14, when the substrate temperatures were respectively 300° C., 450° C., and 500° C., the deposition rates were similar. When the aluminum oxide film was formed by using the aluminum compound represented by Chemical Formula (1) as a precursor, it was confirmed that there was a temperature range allowing the deposition rate to be constant despite changes in the process temperature, and an increase of the deposition rate due to thermal decomposition of the aluminum compound was not observed even at a relatively high temperature of 500° C.

Figure 15:
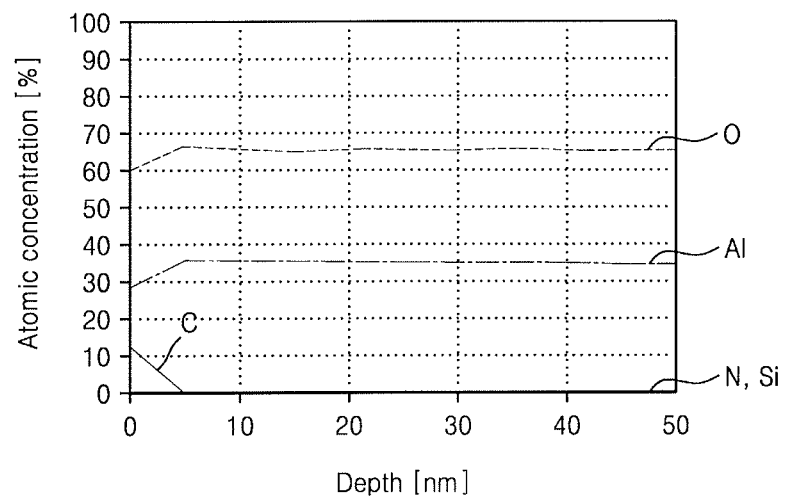
FIG. 15 illustrates a graph depicting X-ray photoelectron spectroscopy (XPS) depth profiling results of the aluminum oxide film formed by using the aluminum compound according to an example embodiment as a precursor.

FIG. 15 is a graph depicting X-ray photoelectron spectroscopy (XPS) depth profiling results for analyzing concentrations of components of the aluminum oxide film formed at a substrate temperature of 500° C. by using the aluminum compound represented by Chemical Formula (1) as a precursor, in Example 3.

It was confirmed that since the amount of carbon atoms detected in the aluminum oxide film obtained by using the aluminum compound represented by Chemical Formula (1) as a precursor was less than about 3 atom %, impurities due to decomposition of the precursor were not generated.

Figure 16:
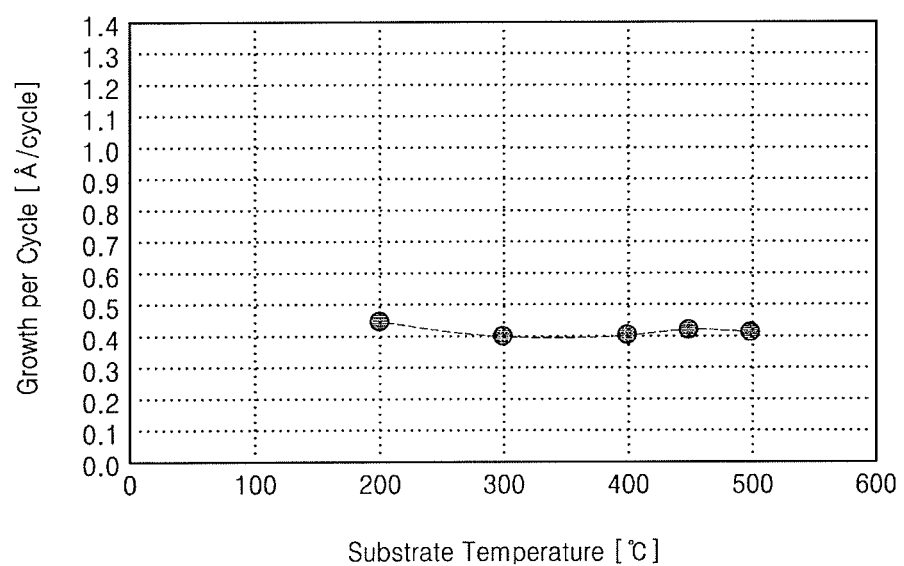
FIG. 16 illustrates a graph depicting measurement results of deposition rate along with process temperature for an aluminum oxide film formed by using an aluminum compound according to an example embodiment as a precursor.

FIG. 16 is a graph depicting measurement results of deposition rate along with process temperature for the aluminum oxide film formed by using the aluminum compound represented by Chemical Formula (2) as a precursor, in Example 3.

As can be seen from FIG. 16, when the substrate temperatures were respectively 200° C., 300° C., 400° C., 450° C., and 500° C., the deposition rates were similar. Therefore, when the aluminum oxide film was formed by using the aluminum compound represented by Chemical Formula (2) as a precursor, it was confirmed that there was a temperature range allowing the deposition rate to be constant regardless of the process temperature, and an increase of the deposition rate due to thermal decomposition of the aluminum compound was not observed even at a relatively high temperature of 500° C.

EXAMPLE 4

Evaluation of thermal decomposition temperature of aluminum compound

The thermal decomposition temperature of each of the aluminum compound represented by Chemical Formula (1) and obtained in Example 1 and the aluminum compound represented by Chemical Formula (2) and obtained in Example 2 was compared with the thermal decomposition temperature of a comparative compound ((di-iso-propyl (methyl)amidinate)diethyl aluminum) represented by Chemical Formula (3).

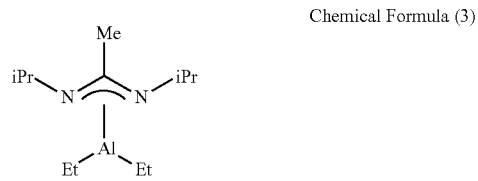

Chemical Formula (3)

For the evaluation of the thermal decomposition temperature, the aluminum compound represented by Chemical Formula (1), the aluminum compound represented by Chemical Formula (2), and the comparative compound represented by Chemical Formula (3) were subjected to DSC analysis. As a result, while the aluminum compounds represented by Chemical Formulae (1) and (2) respectively had relatively high thermal decomposition temperatures (exothermal points) of 396° C. and 403° C., the comparative compound represented by Chemical Formula (3) had a relatively low thermal decomposition temperature of 353° C.

The comparative compound represented by Chemical Formula (3) includes an iPr group and thus has one hydrogen atom at a β-position with respect to an Al atom. Without being bound by theory, it is believed that the hydrogen atom at the (β-position ((β-H) induces β-H elimination with increasing temperature, whereby a bond between a central metal and an N ligand (Al-N) may be broken. As a result, the thermal decomposition temperature of the comparative compound may be reduced due to deterioration of thermal stability of the comparative compound.

On the other hand, each of the aluminum compounds represented by Chemical Formulae (1) and (2) has no hydrogen atom at the β-position and each of the aluminum compounds has a higher thermal decomposition temperature than the comparative compound. Therefore, even though an ALD process is performed at a temperature of about 400° C. or more by using the aluminum compound according to the present example embodiment, ALD deposition properties may be satisfied. In addition, since an aluminum-containing film may be formed by a relatively high temperature process, amounts of undesired impurities in the aluminum-containing film may be reduced. Therefore, the aluminum-containing film can exhibit improved film properties and improved step coverage even in the case of a high aspect ratio.

By way of summation and review, there is a need for a raw material compound for forming thin films, the raw material capable of being subjected to a process of forming a thin film at relatively high temperatures while allowing impurities not to remain in the thin film by securing thermal stability upon the formation of the thin film containing aluminum.

As described above, embodiments relate to an aluminum compound, which is a liquid at room temperature, and methods of forming a thin film and fabricating an integrated circuit device by using the same. Embodiments may provide an aluminum compound capable of suppressing undesired impurities in an aluminum-containing thin film upon formation of the aluminum-containing thin film by using the aluminum compound as a source material and providing excellent thermal stability, process stability, and mass productivity. Embodiments may also provide a method of forming an aluminum-containing thin film, which may suppress undesired impurities in the aluminum-containing thin film and can provide excellent process stability and mass productivity, and a method of fabricating an integrated circuit device, which may provide excellent electrical properties by using the method of forming the aluminum-containing thin film.

According to embodiments, the aluminum compound is in a liquid state at room temperature and may provide extremely excellent thermal stability, and handling and transfer of the aluminum compound may be facilitated. The aluminum compound may be used as a thin film forming material for fabricating an integrated circuit device. In addition, the aluminum compound may suppress foreign substances such as carbon residues remaining in a thin film.

Thus, an aluminum-containing film of good quality may be obtained. According to embodiments, an aluminum-containing film may be formed by using process conditions having an advantage in terms of process stability and mass productivity, and thus, an integrated circuit device capable of providing excellent electrical properties may be fabricated.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A method of forming a thin film, comprising: forming an aluminum-containing film on a substrate by using an aluminum compound represented by one of Chemical Formula (1) and Chemical Formula (2):

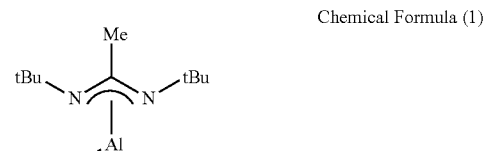

Chemical Formula (1)

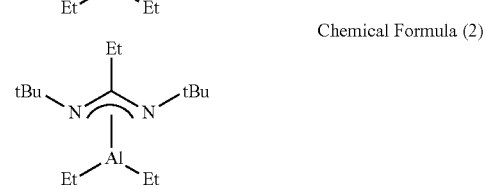

Chemical Formula (2)

wherein Me is a methyl group, Et is an ethyl group, and tBu is a tertiary butyl group.

2. The method as claimed in claim 1, wherein the forming of the aluminum-containing film is performed at a temperature of about 300° C. to about 600° C.

3. The method as claimed in claim 1, wherein the aluminum-containing film is an aluminum oxide film, an aluminum nitride film, or an aluminum alloy film including carbon.

4. A method of fabricating an integrated circuit device, comprising:
    forming a lower structure on a substrate; and
    forming an aluminum-containing film on the lower structure at a temperature of about 300° C. to about 600° C. by using an aluminum compound represented by one of Chemical Formula (1) and Chemical Formula (2):

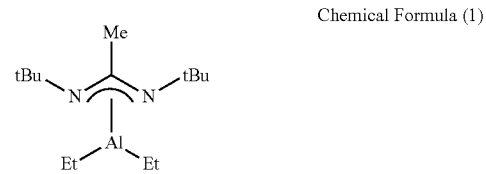

Chemical Formula (1)

Chemical Formula (2)

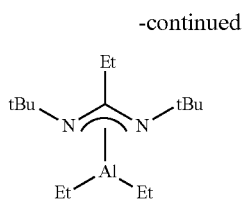

wherein Me is a methyl group, Et is an ethyl group, and tBu is a tertiary butyl group.

5. The method as claimed in claim 4, wherein the forming of the lower structure includes:
   alternately stacking a plurality of insulating layers and a plurality of sacrificial layers on the substrate, layer by layer, the plurality of insulating layers and the plurality of sacrificial layers extending parallel to the substrate;
   forming an opening, which penetrates the plurality of sacrificial layers and the plurality of insulating layers and exposes the plurality of sacrificial layers; and
   forming a plurality of gate spaces in such a manner that one gate space is arranged between two adjacent insulating layers of the plurality of insulating layers, by removing the plurality of sacrificial layers through the opening, and
   the forming of the aluminum-containing film includes:
   forming an aluminum oxide film at a first temperature selected from a range of about 300° C. to about 600° C. by supplying the aluminum compound through the opening, the aluminum oxide film covering inner walls of the plurality of gate spaces and exposed sidewalls of the plurality of insulating layers in the opening.

6. The method as claimed in claim 5, further comprising:
   densifying the aluminum oxide film by annealing the aluminum oxide film at a second temperature that is higher than the first temperature, after the formation of the aluminum oxide film.

7. The method as claimed in claim 5, further comprising:
   forming a conductive film, after the formation of the aluminum oxide film, the conductive film filling the plurality of gate spaces surrounded by the aluminum oxide film; and
   forming a blocking insulating film and a gate electrode in each of the plurality of gate spaces by partially removing the aluminum oxide film and the conductive film in the opening, the blocking insulating film being a portion of the aluminum oxide film, and the gate electrode being a portion of the conductive film.

8. The method as claimed in claim 4, further comprising:
   forming a capacitor on the substrate, the capacitor including a lower electrode, a dielectric film, and an upper electrode,
   wherein the forming of the lower structure includes forming the lower electrode of the capacitor on the substrate, and
   the forming of the aluminum-containing film includes forming an aluminum oxide film to form the dielectric film, the aluminum oxide film covering a surface of the lower electrode.

9. The method as claimed in claim 8, wherein the forming of the capacitor includes forming a high-K dielectric film including a combination of the aluminum-containing film and at least one metal oxide film including a different metal from aluminum to form the dielectric film.

10. The method as claimed in claim 4, wherein the forming of the lower structure includes:
    forming a fin-type active region by partially etching the substrate, the fin-type active region protruding upwards from the substrate; and
    forming a high-K dielectric film on the fin-type active region, and
    the forming of the aluminum-containing film includes forming an Al alloy conductive film at a temperature of about 300° C. to about 600° C. by using the aluminum compound represented by General Formula (I) and a metal compound including a different metal from aluminum, the Al alloy conductive film covering an upper surface and both sidewalls of the fin-type active region, with the high-K dielectric film interposed between the fin-type active region and the Al alloy conductive film.

11. A method of synthesizing an aluminum compound represented by the following General Formula (I), the method comprising:
    combining an alkyllithium compound with a carbodiimide compound, and, subsequently, adding a dialkylaluminum halide compound thereto, the aluminum compound represented by General Formula (I) being the reaction product of the alkyllithium compound, the carbodiimide compound, and the dialkylaluminum halide compound, or
    combining a trialkylaluminum complex with a carbodiimide compound, the aluminum compound represented by General Formula (I) being the reaction product of the trialkylaluminum complex and the carbodiimide compound, General Formula (I)

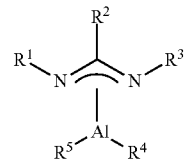

wherein, in General Formula (I):
$R^1$ and $R^3$ are each independently a C4 to C10 branched alkyl, alkenyl, or alkynyl group, or a C4 to C20 substituted or unsubstituted aromatic or alicyclic hydrocarbon group; and
$R^2$, $R^4$, and $R^5$ are each independently a C1 to C10 linear or branched alkyl, alkenyl, or alkynyl group, or a C6 to C20 substituted or unsubstituted aromatic or alicyclic hydrocarbon group.

12. The method as claimed in claim 11, wherein the aluminum compound is synthesized by combining the alkyllithium compound with the carbodiimide compound, and, subsequently, adding the dialkylaluminum halide compound thereto.

13. The method as claimed in claim 12, wherein the carbodiimide compound is di-tert-butyl carbodiimide.

14. The method as claimed in claim 11, wherein the aluminum compound is synthesized by combining the trialkylaluminum complex with the carbodiimide compound.

15. The method as claimed in claim 14, wherein the trialkylaluminum complex is triethyl aluminum and the carbodiimide compound is di-tert-butyl carbodiimide.

16. The method as claimed in claim 12, wherein the alkylithium compound is methyllithium and the dialkylaluminum halide compound is a diethylaluminum halide.

* * * * *